United States Patent
Tanaka

(10) Patent No.: US 10,793,497 B2
(45) Date of Patent: Oct. 6, 2020

(54) DIHYDROXYBIPHENYL COMPOUND, BISPHOSPHITE COMPOUND, CATALYST, PRODUCTION METHOD OF ALDEHYDES, AND PRODUCTION METHOD OF ALCOHOL

(71) Applicant: Mitsubishi Chemical Corporation, Chiyoda-ku (JP)

(72) Inventor: Yoshiyuki Tanaka, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/794,316

(22) Filed: Feb. 19, 2020

(65) Prior Publication Data
US 2020/0181048 A1 Jun. 11, 2020

Related U.S. Application Data

(63) Continuation of application No. PCT/JP2018/031243, filed on Aug. 23, 2018.

(30) Foreign Application Priority Data

Aug. 24, 2017 (JP) ................................. 2017-160759

(51) Int. Cl.
| | | |
|---|---|---|
| C07C 29/153 | (2006.01) | |
| C07F 9/145 | (2006.01) | |
| B01J 31/18 | (2006.01) | |
| C07C 45/50 | (2006.01) | |

(52) U.S. Cl.
CPC ........... *C07C 29/153* (2013.01); *B01J 31/185* (2013.01); *C07C 45/505* (2013.01); *C07F 9/145* (2013.01); *B01J 2231/321* (2013.01); *B01J 2531/822* (2013.01)

(58) Field of Classification Search
CPC .... C07C 29/153; C07C 45/505; B01J 31/185; B01J 2231/321; B01J 2531/822; C07F 9/145
USPC .......................................................... 558/156
See application file for complete search history.

(56) References Cited

U.S. PATENT DOCUMENTS

| | | | |
|---|---|---|---|
| 3,253,915 A * | 5/1966 | Weyerts .................. | G03C 8/16 430/239 |
| 4,748,261 A | 5/1988 | Billig et al. | |
| 4,885,401 A | 12/1989 | Billig et al. | |
| 5,235,113 A | 8/1993 | Sato et al. | |
| 5,312,996 A | 5/1994 | Packett | |
| 5,391,801 A | 2/1995 | Sato et al. | |
| 5,512,696 A | 4/1996 | Kreutzer et al. | |
| 5,663,369 A | 9/1997 | Kreutzer et al. | |
| 5,910,600 A | 6/1999 | Urata et al. | |
| 2012/0190894 A1 | 7/2012 | Wegman | |

| | | | |
|---|---|---|---|
| 2016/0159839 A1 | 6/2016 | Dyballa et al. | |
| 2017/0129838 A1 | 5/2017 | Dyballa et al. | |
| 2018/0319727 A1 | 11/2018 | Dyballa et al. | |

FOREIGN PATENT DOCUMENTS

| | | |
|---|---|---|
| CN | 105967980 A | 9/2016 |
| DE | 11 122 82 B | 8/1961 |
| EP | 3 293 190 A1 | 3/2018 |
| EP | 1 008 580 | 6/2020 |

(Continued)

OTHER PUBLICATIONS

International Search Report dated Oct. 2, 2018 in PCT/JP2018/031243 (with English translation), 9 pages.
Written Opinion of the International Searching Authority dated Oct. 2, 2018 in PCT/JP2018/031243, 7 pages.
Combined Gulf Cooperation Council Office Action and Search Report dated Feb. 11, 2020 in Gulf Cooperation Council Patent Application No. 2018-35895, 6 pages.

(Continued)

*Primary Examiner* — Kristin A Vajda
(74) *Attorney, Agent, or Firm* — Oblon, McClelland, Maier & Neustadt, L.L.P.

(57) ABSTRACT

An object of the present invention is to provide a bisphosphite compound giving higher selectivity for the target product with maintaining a high reaction rate. The present invention relates to a dihydroxybiphenyl compound represented by the following formula (1) and a bisphosphite compound represented by the following formula (2):

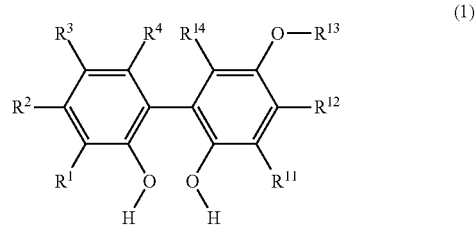

(1)

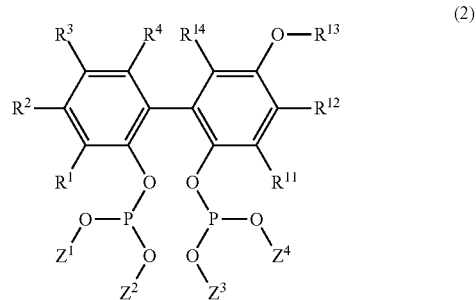

(2)

wherein in formulae (1) and (2), each of $R^1$ to $R^4$, $R^{11}$ to $R^{14}$, and $Z^1$ to $Z^4$ is the same as defined in the description.

15 Claims, No Drawings

(56) References Cited

FOREIGN PATENT DOCUMENTS

| GB | 2450927 A | 1/2009 |
|---|---|---|
| JP | 62-116587 A | 5/1987 |
| JP | 5-178779 A | 7/1993 |
| JP | 6-184036 A | 7/1994 |
| JP | 10-506911 T | 7/1998 |
| JP | 2001-213835 | 8/2001 |
| JP | 3812046 B2 | 8/2006 |
| JP | 2013-508274 A | 3/2013 |
| JP | 2015-182992 A | 10/2015 |
| JP | 2016-108333 A | 6/2016 |
| JP | 2017-125005 A | 7/2017 |
| WO | WO 2017/083702 A1 | 5/2017 |

OTHER PUBLICATIONS

Lebeuf, R., et al., Hydroquinone-Based Biarylic Polyphenols as Redox Organocatalysts for Dioxygen Reduction: Dramatic Effect of Orcinol Substituent on the Catalytic Activity, Advanced Synthesis & Catalysis, Jan. 16, 2017, vol. 359, pp. 268-278.

Kamitanaka, T., et al., "Efficient Coupling Reaction of Quinone Monoacetal with Phenols Leading to Phenol Biaryls", Angewandte Chemie International Edition, 2016, vol. 55, pp. 15535-15538.

Quell, T., et al., "Facile and Selective Cross-Coupling of Phenols Using Selenium Dioxide", European Journal of Organic Chemistry, 2016, pp. 4307-4310.

Gao, H., et al., "Practical Organocatalytic Synthesis of Functionalized Non-$C_2$-Symmetrical Atropisomeric Biaryls", Angewandte Chemie International Edition, 2016, vol. 55, pp. 566-571.

Libman, A., et al., "Synthetic and Predictive Approach to Unsymmetrical Biphenols by Iron-Catalyzed Chelated Radical-Anion Oxidative Coupling", Journal of the American Chemical Society, 2015, vol. 137, pp. 11453-11460.

Dohi, T., et al., "Coupling of Quinone Monoacetals Promoted by Sandwiched Brønsted Acids: Synthesis of Oxygenated Biaryls**", Angewandte Chemie International Edition, 2011, vol. 50, pp. 6142-6146.

Liang, Y., et al., "Generation of Self-Supported Noyori-Type Catalysts Using Achiral Bridged-BIPHEP for Heterogeneous Asymmetric Hydrogenation of Ketones", Advanced Synthesis & Catalysis, 2006, vol. 348, pp. 1533-1538.

Sartori, G., et al., "Selective Synthesis of Unsymmetrical Hydroxylated and Methoxylated Biaryls", Journal of Organic Chemistry, 1993, vol. 58, pp. 7271-7273.

Hewgill, F. R., et al., "Oxidation of Alkoxyphenols. Part 28.[1] On the Configuration of 2,2'-Diphenoquinones", J. Chem. Soc. Perkin Trans. I, 1983, pp. 131-134.

Sartori, G., et al., "Reinvestigation of the Pummerer Arylation of Quinones: A Selective Approach to 2,2' , 5'-Trihydroxybiaryls", J. Chem. Soc. Perkin Trans. 1, 1993, pp. 39-42.

Hewgill, F. R., et al., "Oxidation of Alkoxyphenols. XXI* Oxidative Cross-Coupling of Phenols to Unsymmetrical Biphenyl-2,2'-diols", Aust. J. Chem., 1978, vol. 31, pp. 1061-1068.

Leupold, I., et al., "Über Signalverschiebungen in den NMR-Spektren von tert.-Butyl-, tert.-Butyloxy- und Nitro-tert.-butylbenzolderivaten durch aromatische Lösungsmittel", Chem. Ber., 1971, vol. 104, pp. 40-49.

European Search Report as received in the corresponding Patent Application No. 18848171.07-1109/ 3674282 PCT/JP2018031243 dated Jul. 22, 2020.

* cited by examiner

DIHYDROXYBIPHENYL COMPOUND, BISPHOSPHITE COMPOUND, CATALYST, PRODUCTION METHOD OF ALDEHYDES, AND PRODUCTION METHOD OF ALCOHOL

TECHNICAL FIELD

The present invention relates to a novel dihydroxybiphenyl compound, a novel bisphosphite compound as a derivative of the dihydroxybiphenyl compound, a catalyst containing the bisphosphite compound, a production method of aldehydes using the bisphosphite compound, and a production method of an alcohol using the aldehydes.

BACKGROUND ART

A method for producing aldehydes or alcohols as hydrogenated products thereof by reacting an olefinic compound with synthesis gas (mixed gas of CO and $H_2$) in the presence of a catalyst is well-known as a hydroformylation process (reaction). As the catalyst for the hydroformylation reaction, a soluble complex with a metal of Group 8 of the periodic table, containing an organic phosphorus compound as a ligand, is usually used.

In general, the ligand used together with the metal component of the catalyst significantly affects the catalytic reaction. In the hydroformylation reaction, it is also widely known that the reaction activity and selectivity are greatly changed by the ligand. In order to advantageously conduct the hydroformylation reaction in industry, enhancement of the reaction activity and selectivity is an important issue and therefore, ligand designs are being actively pursued.

Various phosphite compounds are known as a group of phosphorus compounds utilized as the ligand for the hydroformylation reaction. As for various phosphite compounds, in addition to simple monophosphites such as trialkyl phosphite and triarylphosphite, polyphosphites, etc. having a plurality of coordinating phosphorus atoms in the molecule have been proposed.

For example, Patent Document 1 discloses a bisphosphite compound in which one of two phosphite groups has a cyclic structure. In addition, Patent Document 2 discloses a bisphosphite compound in which both of two phosphite groups have a cyclic structure.

On the other hand, Patent Document 3 discloses a bisphosphite compound in which both of two phosphite groups are not cyclized. In this bisphosphite compound, the substituent on the bisarylene group in the crosslinking moiety is not specified. Furthermore, as four ester terminal groups, a phenyl group having a hydrocarbon substituent at least in the ortho position or a β-naphthyl group having a hydrocarbon substituent at least in the 3-position is used. As the hydrocarbon substituent, a bulky organic group having a carbon number of 3 or more, such as isopropyl group and tertiary butyl group, is used.

BACKGROUND ART LITERATURE

Patent Document

[Patent Document 1] JP-A-S62-116587
[Patent Document 2] JP-A-H06-184036
[Patent Document 3] JP-A-H05-178779

SUMMARY OF THE INVENTION

Problems that the Invention is to Solve

In this way, various phosphite compounds have been proposed as the ligand for use in the hydroformylation reaction. However, in the hydroformylation reaction using bisphosphite compounds reported so far, when a high reaction rate is obtained, the selectivity for linear aldehyde as the target product is insufficient, and on the contrary, when high selectivity for linear aldehyde is obtained, the reaction rate is insufficient.

In the hydroformylation reaction using a bisphosphite compound, from the viewpoint of improving the economic efficiency in commercial production, it is very important to satisfy both a high reaction rate and high selectivity for the target product. Accordingly, it has been keenly demanded to develop a bisphosphite ligand giving higher selectivity for the target product with maintaining a high reaction rate.

Means for Solving the Problems

In the course of intensively studying a ligand for enhancing and maintaining both reaction activity and selectivity for the target product in the hydroformylation reaction, the inventors of the present invention have discovered a novel dihydroxybiphenyl compound having a specific structure, and a novel bisphosphite compound as a derivative of the dihydroxybiphenyl compound, and found that when this bisphosphite compound is employed as a ligand used together with one component, namely, metal component of the catalyst in the hydroformylation reaction, that is, the metal component of the catalyst, the reaction proceeds at a high rate and very excellent selectivity for the target product is obtained. The present invention has been accomplished based on this finding.

More specifically, the gist of the present invention is as follows.

(1) A dihydroxybiphenyl compound represented by the following formula (1):

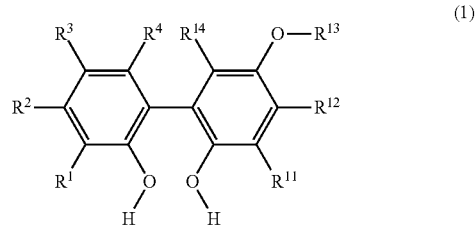

wherein in formula (1), each of $R^1$ and $R^{11}$ independently represents a member selected from the group consisting of a hydrogen atom, an alkyl group having from 1 to 20 carbon atoms, and a cycloalkyl group having from 3 to 20 carbon atoms;

each of $R^2$ and $R^{12}$ independently represents a member selected from the group consisting of a hydrogen atom, an alkyl group having from 1 to 20 carbon atoms, an alkoxy group having from 1 to 20 carbon atoms, a cycloalkyl group having from 3 to 20 carbon atoms, a cycloalkoxy group having from 3 to 20 carbon atoms, a dialkylamino group having from 2 to 20 carbon atoms, an aryl group having from 6 to 20 carbon atoms, an aryloxy group having from 6 to 20 carbon atoms, an alkylaryl group having from 7 to 20 carbon atoms, an alkylaryloxy group having from 7 to 20 carbon atoms, an arylalkyl group having from 7 to 20 carbon atoms, an arylalkoxy group having from 7 to 20 carbon atoms, a cyano group, a hydroxy group, and a halogen atom;

each of $R^3$ and $R^{13}$ independently represents a member selected from the group consisting of a hydrogen atom, an alkyl group having from 1 to 20 carbon atoms, a cycloalkyl group having from 3 to 20 carbon atoms, an aryl group having from 6 to 20 carbon atoms, an alkylaryl group having from 7 to 20 carbon atoms, and an arylalkyl group having from 7 to 20 carbon atoms; and each of $R^4$ and $R^{14}$ independently represents a member selected from the group consisting of a hydrogen atom, an alkyl group having from 1 to 12 carbon atoms, a cycloalkyl group having from 3 to 12 carbon atoms, an alkoxy group having from 1 to 12 carbon atoms, a silyl group, a siloxy group, and a halogen atom.

(2) A bisphosphite compound represented by the following formula (2):

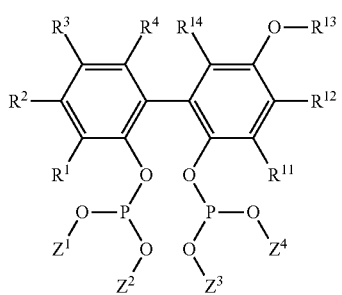

wherein in formula (2), each of $R^1$ and $R^{11}$ independently represents a member selected from the group consisting of a hydrogen atom, an alkyl group having from 1 to 20 carbon atoms, and a cycloalkyl group having from 3 to 20 carbon atoms;

each of $R^2$ and $R^{12}$ independently represents a member selected from the group consisting of a hydrogen atom, an alkyl group having from 1 to 20 carbon atoms, an alkoxy group having from 1 to 20 carbon atoms, a cycloalkyl group having from 3 to 20 carbon atoms, a cycloalkoxy group having from 3 to 20 carbon atoms, a dialkylamino group having from 2 to 20 carbon atoms, an aryl group having from 6 to 20 carbon atoms, an aryloxy group having from 6 to 20 carbon atoms, an alkylaryl group having from 7 to 20 carbon atoms, an alkylaryloxy group having from 7 to 20 carbon atoms, an aryl alkyl group having from 7 to 20 carbon atoms, an arylalkoxy group having from 7 to 20 carbon atoms, a cyano group, a hydroxy group, and a halogen atom;

each of $R^3$ and $R^{13}$ independently represents a member selected from the group consisting of a hydrogen atom, an alkyl group having from 1 to 20 carbon atoms, a cycloalkyl group having from 3 to 20 carbon atoms, an aryl group having from 6 to 20 carbon atoms, an alkylaryl group having from 7 to 20 carbon atoms, and an arylalkyl group having from 7 to 20 carbon atoms;

each of $R^4$ and $R^{14}$ independently represents a member selected from the group consisting of a hydrogen atom, an alkyl group having from 1 to 12 carbon atoms, a cycloalkyl group having from 3 to 12 carbon atoms, an alkoxy group having from 1 to 12 carbon atoms, a silyl group, a siloxy group, and a halogen atom; and each of $Z^1$ to $Z^4$ independently represents an aryl group having from 6 to 20 carbon atoms and may have a substituent, and both of paired $Z^1$ and $Z^2$ and paired $Z^3$ and $Z^4$ are not combined.

(3) The bisphosphite compound according to (2), wherein each of $R^1$ and $R^{11}$ independently represents a tertiary alkyl group having from 4 to 20 carbon atoms, $R^2$ and $R^{12}$ represent a hydrogen atom, each of $R^3$ and $R^{13}$ independently represents a tertiary alkyl group having from 4 to 20 carbon atoms, each of $R^4$ and $R^{14}$ independently represents a member selected from the group consisting of an alkyl group having from 1 to 3 carbon atoms, an alkoxy group having from 1 to 3 carbon atoms, and a halogen atom.

(4) The bisphosphite compound according to (3), wherein each of $Z^1$ to $Z^4$ independently represents an aryl group having no substituent on the aromatic ring carbon atom adjacent to the carbon atom bonded to oxygen atom or an aryl group having a substituent having from 1 to 2 carbon atoms on the aromatic ring carbon atom.

(5) The bisphosphite compound according to (4), wherein each of $R^1$, $R^{11}$, $R^3$ and $R^{13}$ independently represents a tertiary alkyl group having from 4 to 7 carbon atoms and each of $R^4$ and $R^{14}$ independently represents an alkyl group having from 1 to 3 carbon atoms.

(6) The bisphosphite compound according to (5), wherein each of $Z^1$ to $Z^4$ independently represents a 1-naphthyl group or a 2-naphthyl group.

(7) The bisphosphite compound according to (6), wherein $R^1$, $R^{11}$, $R^3$ and $R^{13}$ represent a tert-butyl group and $R^4$ and $R^{14}$ represent a methyl group.

(8) A catalyst comprising a complex of the bisphosphite compound according to any one of (2) to (7) and a metal of Groups 8 to 10.

(9) The catalyst according to (8), wherein a molar ratio of the bisphosphite compound to the metal of Groups 8 to 10 is from 0.00004 to 500.

(10) The catalyst according to (8), wherein a molar ratio of the bisphosphite compound to the metal of Groups 8 to 10 is from 0.0002 to 100.

(11) The catalyst according to (8), wherein a molar ratio of the bisphosphite compound to the metal of Groups 8 to 10 is from 0.001 to 50.

(12) A method for producing aldehydes, comprising reacting an olefin compound with carbon monoxide and hydrogen in the presence of a compound of a metal of Groups 8 to 10 and the bisphosphite compound according to any one of (2) to (7).

(13) The production method of aldehydes according to (12), wherein a concentration of the compound of a metal of Groups 8 to 10 in a reaction solution is from 0.05 to 5,000 mg/L in terms of metal atoms.

(14) A method for producing aldehydes, comprising reacting an olefin compound with carbon monoxide and hydrogen in the presence of the catalyst according to any one of (8) to (11).

(15) A method for producing an alcohol, comprising producing aldehydes by the production method of aldehydes according to any one of (12) to (14), and then reacting the aldehydes with hydrogen.

(16) The dihydroxybiphenyl compound according to (1), wherein each of $R^1$ and $R^{11}$ independently represents a tertiary alkyl group having from 4 to 20 carbon atoms, $R^2$ and $R^{12}$ represent a hydrogen atom, each of $R^3$ and $R^{13}$ independently represents a tertiary alkyl group having from 4 to 20 carbon atoms, and each of $R^4$ and $R^{14}$ independently represents a member selected from the group consisting of an alkyl group having from 1 to 3 carbon atoms, an alkoxy group having from 1 to 3 carbon atoms, and a halogen atom.

(17) The dihydroxybiphenyl compound according to (16), wherein each of $R^1$, $R^{11}$, $R^3$ and $R^{13}$ independently represents a tertiary alkyl group having from 4 to 7 carbon atoms and each of $R^4$ and $R^{14}$ independently represents an alkyl group having from 1 to 3 carbon atoms.

(18) The dihydroxybiphenyl compound according to (17), wherein $R^1$, $R^{11}$, $R^3$ and $R^{13}$ represent a tert-butyl group and $R^4$ and $R^{14}$ represent a methyl group.

Effect of the Invention

The dihydroxybiphenyl compound and bisphosphite compound of the present invention are novel compounds that can be used as a constituting element of a homogeneous metal catalyst for various organic reactions such as hydrogenation, hydroformylation, hydrocyanation, hydrocarboxylation, hydroamidation, hydroesterification and aldol condensation.

Furthermore, in the production method of aldehydes of the present invention, the bisphosphite compound of the present invention is used as a catalyst component in the hydroformylation reaction, and not only high reactivity but also very high selectivity for aldehyde isomers is thereby obtained, so that production of aldehyde can be industrially advantageously conducted.

MODE FOR CARRYING OUT THE INVENTION

Although the embodiment of the present invention is described in detail below, description of the constituting elements described below is one example of the embodiment of the present invention, and the present invention is not limited to these contents.

[Dihydroxybiphenyl Compound and Bisphosphite Compound]

The novel dihydroxybiphenyl compound and bisphosphite compound of the present invention are compounds represented by the following formulae (1) and (2), respectively.

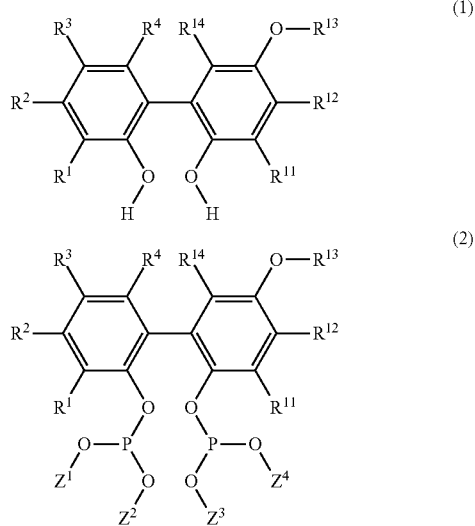

In formulae (1) and (2), each of $R^1$ and $R^{11}$ independently represents a member selected from the group consisting of a hydrogen atom, an alkyl group having from 3 to 20 carbon atoms, and a cycloalkyl group.

The alkyl group having from 1 to 20 carbon atoms includes, for example, a linear or branched alkyl group such as methyl group, ethyl group, n-propyl group, i-propyl group, s-butyl group, tert-butyl group, isopentyl group, neopentyl group, tert-pentyl group, tert-hexyl group and 1,1,2-trimethylpropyl group. Among these, an alkyl group having from 3 to 20 carbon atoms is preferred, an alkyl group having from 4 to 20 carbon atoms is more preferred, and an alkyl group having from 4 to 10 carbon atoms is particularly preferred. Furthermore, an alkyl group in which the carbon atom bonded to the aromatic ring is a tertiary carbon atom is preferred, and examples thereof include a tert-butyl group, a tert-pentyl group, and a tert-hexyl group.

Examples of a cycloalkyl group having a carbon number of 3 to 20 include cyclohexyl group, cyclooctyl group and adamantyl group. Among those, a cycloalkyl group having a carbon number of 6 to 14 is preferable and a cycloalkyl group having a carbon number of 6 to 10 is more preferable.

$R^1$ and $R^{11}$ are preferably a tertiary alkyl group having from 4 to 20 carbon atoms, more preferably a tertiary alkyl group having from 4 to 7 carbon atoms, particularly preferably a tert-butyl group. $R^1$ and $R^{11}$ may be the same as or different from each other.

When $R^1$ and $R^{11}$ are a tert-butyl group, the compound represented by formula (1) can be easily synthesized by reacting an inexpensive raw material such as isobutylene gas or tert-butyl alcohol with phenols such as phenol or cresol which becomes a raw material of the compound. In addition, when $R^1$ and $R^{11}$ are a tert-butyl group, the effect of stabilizing the compound represented by formula (2) against hydrolysis is sufficiently obtained due to bulkiness of the tert-butyl group. For these reasons, $R^1$ and $R^{11}$ are preferably a tert-butyl group, among others.

Each of $R^2$ and $R^{12}$ independently represents a member selected from the group consisting of a hydrogen atom, an alkyl group having from 1 to 20 carbon atoms, an alkoxy group having from 1 to 20 carbon atoms, a cycloalkyl group having from 3 to 20 carbon atoms, a cycloalkoxy group having from 3 to 20 carbon atoms, a dialkylamino group having from 2 to 20 carbon atoms, an aryl group having from 6 to 20 carbon atoms, an aryloxy group having from 6 to 20 carbon atoms, an alkylaryl group having from 7 to 20 carbon atoms, an alkylaryloxy group having from 7 to 20 carbon atoms, an arylalkyl group having from 7 to 20 carbon atoms, an arylalkoxy group having from 7 to 20 carbon atoms, a cyano group, a hydroxy group, and a halogen atom.

The alkyl group having from 1 to 20 carbon atoms includes, for example, a linear or branched alkyl group such as methyl group, ethyl group, n-propyl group, i-propyl group, n-butyl group, s-butyl group, tert-butyl group, n-pentyl group, isopentyl group, neopentyl group, tert-pentyl group and tert-hexyl group.

The cycloalkyl group having from 3 to 20 carbon atoms includes, for example, a cyclohexyl group, a cyclooctyl group, and an adamantyl group.

The alkoxy group having from 1 to 20 carbon atoms includes, for example, a methoxy group, an ethoxy group, an isopropoxy group and a tert-butoxy group. Among those, an alkoxy group having a carbon number of 1 to 12 is preferable.

The cycloalkoxy group having from 3 to 20 carbon atoms includes, for example, a cyclopentyloxy group.

The dialkylamino group having from 2 to 20 carbon atoms includes, for example, a dimethylamino group and a diethyl amino group.

The aryl group having from 6 to 20 carbon atoms includes, for example, a phenyl group and a naphthyl group.

The aryloxy group having from 6 to 20 carbon atoms includes, for example, a phenoxy group and a naphthoxy group.

The alkyl aryl group having from 7 to 20 carbon atoms includes, for example, a p-tolyl group and an o-tolyl group.

The alkylaryloxy group having from 7 to 20 carbon atoms includes, for example, a 2,3-xylenoxy group.

The arylalkyl group having from 7 to 20 carbon atoms includes, for example, a benzyl group.

The arylalkoxy group having from 7 to 20 carbon atoms includes, for example, a 2-(2-naphthyl)ethoxy group.

The halogen atom includes, for example, a fluorine atom, a chlorine atom, a bromine atom, and an iodine atom.

$R^2$ and $R^{12}$ may be the same as or different from each other.

$R^2$ and $R^{12}$ are preferably a hydrogen atom. The substituent at this position little contributes to the effect of improving reactivity in the hydroformylation reaction or the effect of stabilizing the compound itself represented by formula (2). Accordingly, from the viewpoint of reducing the production cost of the compound, the substituent is preferably a hydrogen atom that is a simplest substituent.

Each of $R^3$ and $R^{13}$ represents a member selected from the group consisting of a hydrogen atom, an alkyl group having from 1 to 20 carbon atoms, a cycloalkyl group having from 3 to 20 carbon atoms, an aryl group having from 6 to 20 carbon atoms, an alkylaryl and arylalkyl group having from 7 to 20 carbon atoms.

The alkyl group having from 1 to 20 carbon atoms includes, for example, a linear or branched alkyl group such as methyl group, ethyl group, n-propyl group, i-propyl group, s-butyl group, tert-butyl group, isopentyl group, neopentyl group, tert-pentyl group and tert-hexyl group. Among these, an alkyl group having from 4 to 20 carbon atoms is preferred, an alkyl group having from 4 to 10 carbon atoms is more preferred. Furthermore, an alkyl group in which the carbon atom bonded to the aromatic ring is a tertiary carbon atoms is preferred, and examples thereof include a tert-butyl group, a tert-pentyl group, and a tert-hexyl group.

Examples of the cycloalkyl group having a carbon number of 3 to 20 include a cyclohexyl group, cyclooctyl group and adamantyl group. Among those, a cycloalkyl group having a carbon number of 6 to 14 is preferable and a cycloalkyl group having a carbon number of 6 to 10 is more preferable.

The aryl group having a carbon number of 6 to 20 includes, for example, a phenyl group and a naphthyl group.

The alkylaryl group having a carbon number of 7 to 20 includes, for example, a p-tolyl group and an o-tolyl group.

The arylalkyl group having a carbon number of 7 to 20 includes, for example, a benzyl group.

Each of $R^3$ and $R^{13}$ is preferably a tertiary alkyl group having from 4 to 20 carbon atoms, more preferably a tertiary alkyl group having from 4 to 7 carbon atoms, and particularly preferably a tert-butyl group. $R^3$ and $R^{13}$ may be the same as or different from each other.

The reason why a tert-butyl group is particularly preferred is, for example, that the compound represented by formula (1) can be easily synthesized by reacting an inexpensive raw material such as isobutylene gas or tert-butyl alcohol with phenols such as phenol or cresol which becomes a raw material of the compound.

Each of $R^4$ and $R^{14}$ independently represents a member selected from the group consisting of a hydrogen atom, an alkyl group having from 1 to 12 carbon atoms, a cycloalkyl group having from 3 to 12 carbon atoms, an alkoxy group having from 1 to 12 carbon atoms, a silyl group, a siloxy group, and a halogen atom.

The alkyl group having from 1 to 12 carbon atoms includes, for example, a linear or branched alkyl group such as a methyl group, an ethyl group, a n-propyl group, an isopropyl group, a tert-butyl group and a decyl group.

The cycloalkyl group having from 3 to 12 carbon atoms includes for example, a cyclopropyl group and a cyclohexyl group.

The alkoxy group having from 1 to 12 carbon atoms includes, for example, a methoxy group, an ethoxy group and a tert-butoxy group.

The silyl group includes, for example, a trimethylsilyl group.

The siloxy group includes, for example, a silyl group and a trimethylsiloxy group.

The halogen atom includes, for example, a fluorine atom, a chlorine atom, a bromine atom, and an iodine atom.

Among these, each of $R^4$ and $R^{14}$ is independently, preferably an alkyl group having from 1 to 3 carbon atoms, such as methyl group or ethyl group, an alkoxy group having from 1 to 3 carbon atoms, such as methoxy group or ethoxy group, or a halogen atoms, more preferably an alkyl group having from 1 to 3 carbon atoms, and it is particularly preferred that $R^4$ and $R^{14}$ are a methyl group.

The reason why $R^4$ and $R^{14}$ are preferably a small group like an alkyl group having from 1 to 3 carbon atoms, particularly, a methyl group, is that both of smooth progress of the later-described coupling reaction and enhancement of stability of the compound represented by formula (2) can be achieved.

Each of $Z^1$ to $Z^4$ is independently an aryl group having from 6 to 20 carbon atoms, and the aryl group may have a substituent. In this connection, both of paired $Z^1$ and $Z^2$ and paired $Z^3$ and $Z^4$ are not combined.

In particular, each of $Z^1$ to $Z^4$ is independently, preferably an aryl group having no substituent on the aromatic ring carbon atom adjacent to the carbon atom bonded to oxygen atom or an aryl group having a substituent on the aromatic ring carbon atom, with the number of carbon atoms of the substituent being from 0 to 2.

In the case where $Z^1$ to $Z^4$ have a substituent on the aromatic ring carbon atom adjacent to the carbon atom bonded to oxygen atom, each substituent is preferably selected from a group having from 1 to 2 carbon atoms such as a methyl group and an ethyl group, a trifluoromethyl group, a cyano group, a nitro group, and a halogen atom such as chlorine atom and fluorine atom.

In the case where $Z^1$ to $Z^4$ have a substituent at the position other than the aromatic ring carbon atom above, the substituent includes a linear or branched alkyl group having a carbon number of 1 to 12, preferably from 1 to 8, such as methyl group, ethyl group, n-propyl group, i-propyl group, n-butyl group, s-butyl group, tert-butyl group, n-pentyl group, isopentyl group, neopentyl group and tert-pentyl group; an alkoxy group having a carbon number of 1 to 12, preferably from 1 to 8, such as methoxy group and ethoxy group; and an aryl group having a carbon number of 6 to 18, preferably from 6 to 10, such as phenyl group and naphthyl group, and in addition, includes a halogen atom, a cyano group, a nitro group, a trifluoromethyl group, a hydroxyl group, an amino group, an acyl group, a carbonyloxy group, an oxycarbonyl group, an amide group, a sulfonyl group, a sulfinyl group, a silyl group, and a thionyl group. Each one of $Z^1$ to $Z^4$ may have from 1 to 5 of these substituents.

Suitable groups as $Z^1$ to $Z^4$ include a phenyl group, a 1-naphthyl group, a 2-naphthyl group, a p-trifluoromethylphenyl group, a 2-ethylphenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 3,4-dimethylphenyl group, a 3,5-dimethylphenyl group, a 2-chlorophenyl group, a 3-chlorophenyl group, a 4-chlorophenyl group, a 2,3-dichlorophenyl group, a 2,4-dichlorophenyl group, a 2,5-dichlorophenyl group, a 3,4-dichlorophenyl group, a 3,5-dichlorophenyl group, a 2-methoxyphenyl group, a 3-methoxyphenyl group, a 4-methoxyphenyl group, a 2,3-dimethoxyphenyl group, a 3,4-dimethoxyphenyl group, a 3,5-dimethoxyphenyl group, a 4-cyanophenyl group, a 4-nitrophenyl group, a 4-phenylphenyl group, a 5,6,7,8-tetrahydro-1-naphthyl group, a 5,6,7,8-tetrahydro-2-naphthyl group, a 2-methyl-1-naphthyl group, a 4-chloro-1-naphthyl group, a 2-nitro-1-naphthyl group, a 7-methoxy-2-naphthyl group, etc.

Among these, a 1-naphthyl group or a 2-naphthyl group is preferred from the viewpoint of enhancing the thermal stability of the ligand and enhancing the selectivity for the production of linear aldehydes at the time of producing aldehydes by a hydroformylation reaction.

The dihydroxybiphenyl compound represented by formula (1) is preferably a dihydroxybiphenyl compound in which each of $R^1$ and is independently a tertiary alkyl group having from 4 to 20 carbon atoms; each of $R^2$ and $R^{12}$ is a hydrogen atom; each of $R^3$ and $R^{13}$ is a tertiary alkyl group having from 4 to 20 carbon atoms; and each of $R^4$ and $R^{14}$ is independently a member selected from the group consisting of an alkyl group having from 1 to 3 carbon atoms, an alkoxy group having from 1 to 3 carbon atoms, and a halogen atom, more preferably a dihydroxybiphenyl compound in which each of $R^1$, $R^{11}$, $R^3$ and $R^{13}$ is independently a tertiary alkyl group having from 4 to 7 carbon atoms; $R^2$ and $R^{12}$ are a hydrogen atom; and each of $R^4$ and $R^{14}$ is independently an alkyl group having from 1 to 3 carbon atoms, still more preferably a dihydroxybiphenyl compound in which $R^1$, $R^{11}$, $R^3$ and $R^{13}$ are a tert-butyl group; $R^2$ and $R^{12}$ are a hydrogen atom; and $R^4$ and $R^{14}$ are a methyl group.

The bisphosphite compound represented by formula (2) is preferably a bisphosphite compound in which each of $R^1$ and $R^{11}$ is independently a tertiary alkyl group having from 4 to 20 carbon atom; $R^2$ and $R^{12}$ are a hydrogen atom; each of $R^3$ and $R^{13}$ is independently a tertiary alkyl group having from 4 to 20 carbon atoms; and each of $R^4$ and $R^{14}$ is independently a member selected from the group consisting of an alkyl group having from 1 to 3 carbon atoms, an alkoxy group having from 1 to 3 carbon atoms, and a halogen atom, more preferably a bisphosphite compound in which each of $Z^1$ to $Z^4$ independently has no substituent on the aromatic ring carbon atom adjacent to the carbon atom bonded to the oxygen atom or has a substituent having from 1 to 2 carbon atoms on the aromatic ring carbon atoms and all of $Z^1$ to $Z^4$ are not combined with each other.

The bisphosphite compound represented by formula (2) is still more preferably a bisphosphite compound in which each of $R^1$, $R^{11}$, $R^3$ and $R^{13}$ is independently a tertiary alkyl group having from 4 to 7 carbon atoms; $R^2$ and $R^{12}$ are a hydrogen atom; and each of $R^4$ and $R^{14}$ is independently an alkyl group having from 1 to 3 carbon atoms, yet still more preferably a bisphosphite compound in which each of $Z^1$ to $Z^4$ is independently a 1-naphthyl group or a 2-naphthyl group, even yet still more preferably a bisphosphite compound in which $R^1$, $R^{11}$, $R^3$ and $R^{13}$ are a tert-butyl group; and $R^4$ and $R^{14}$ are a methyl group.

Examples of the bisphosphite compound represented by formula (2) are set forth below. The sign in each of the following formulae has the following meaning.

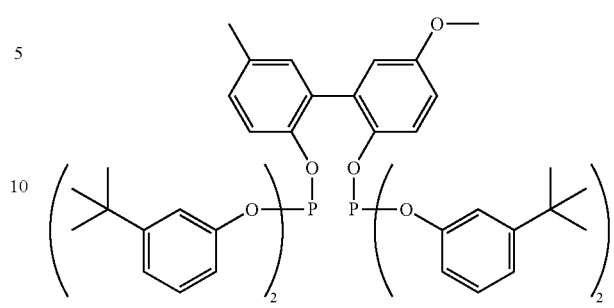

(L-1)

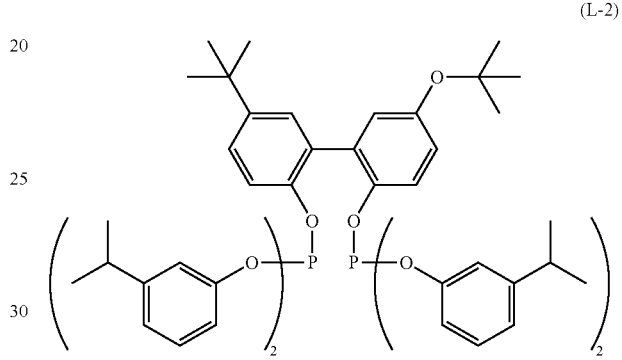

(L-2)

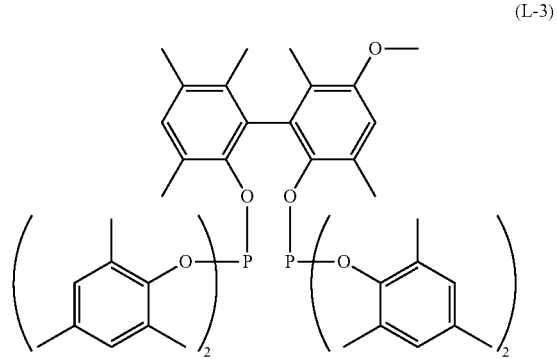

(L-3)

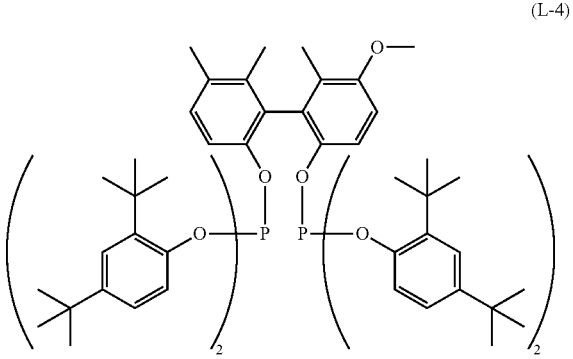

(L-4)

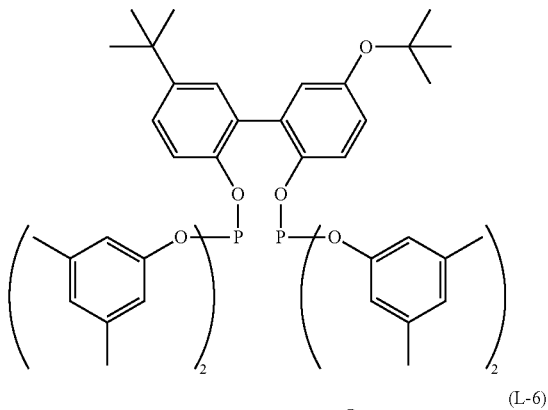

(L-13) 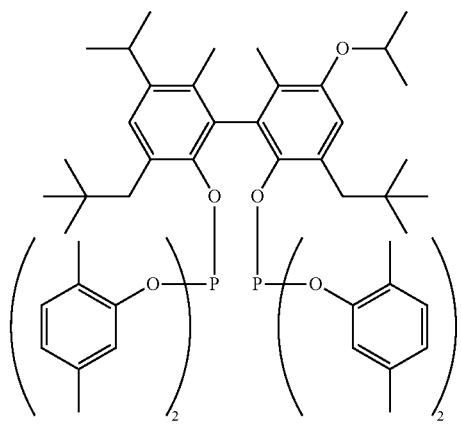
(L-14) 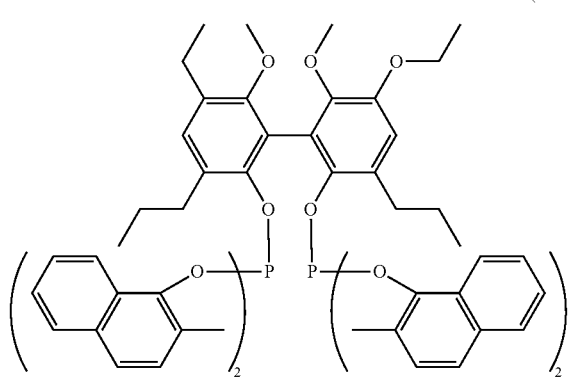
(L-15) 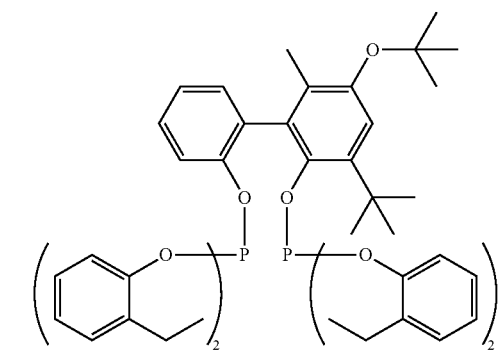
(L-26) 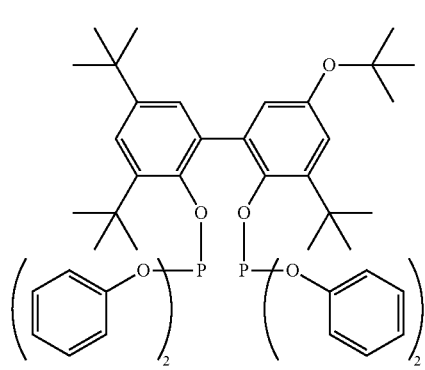
(L-27) 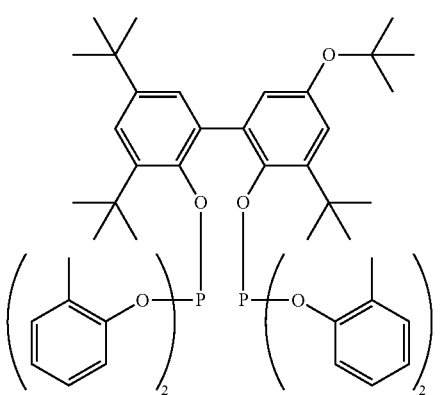
(L-28) 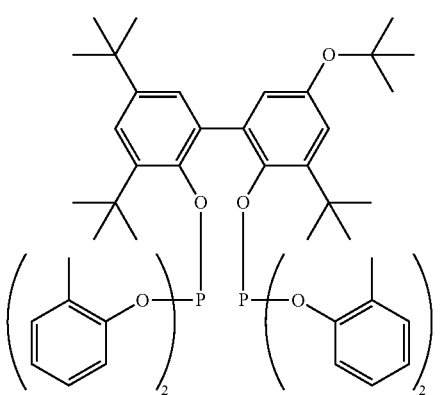
(L-29) 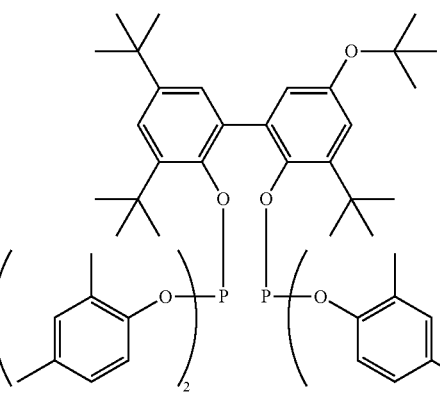
(L-30) 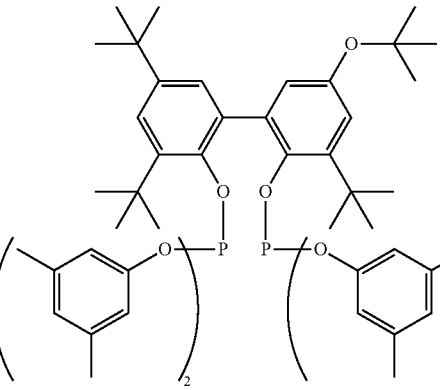

(L-31)
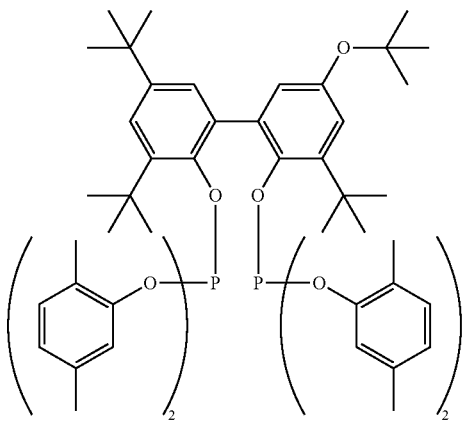
(L-32)
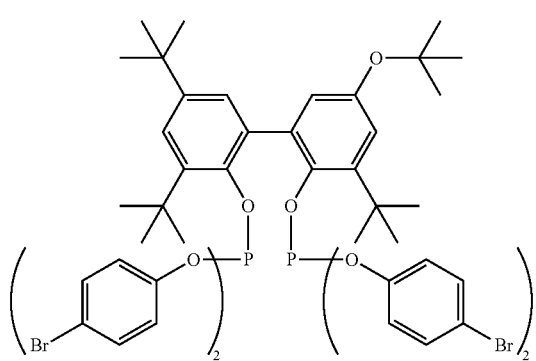
(L-33)
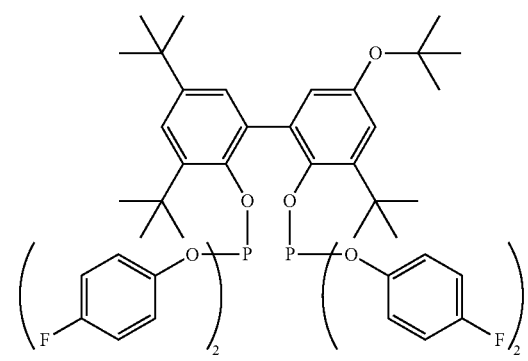
(L-34)
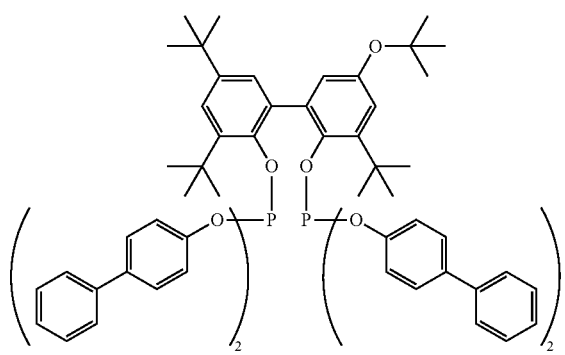
(L-35)
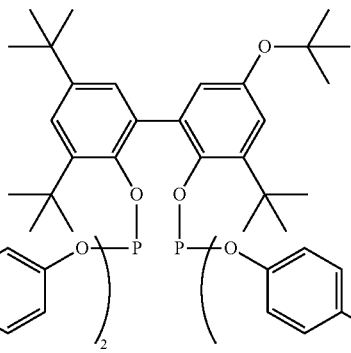
(L-36)
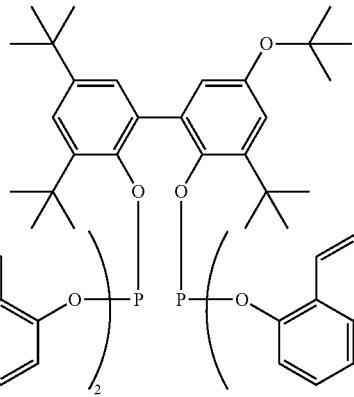
(L-37)
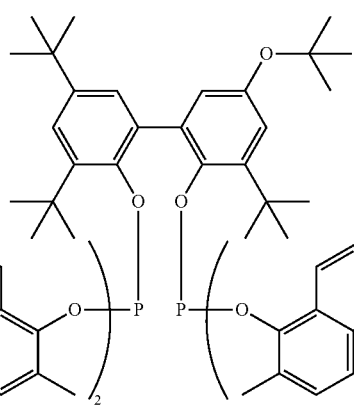
(L-38)
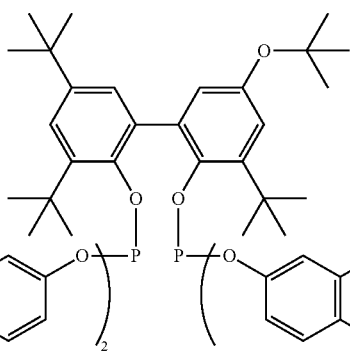

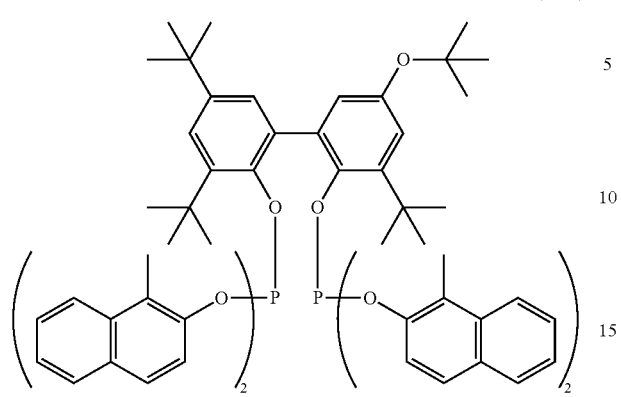
(L-39)
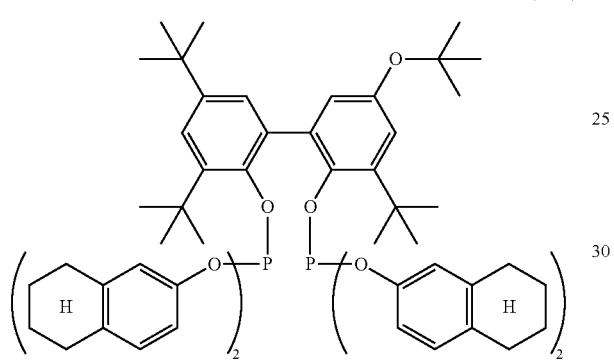
(L-40)
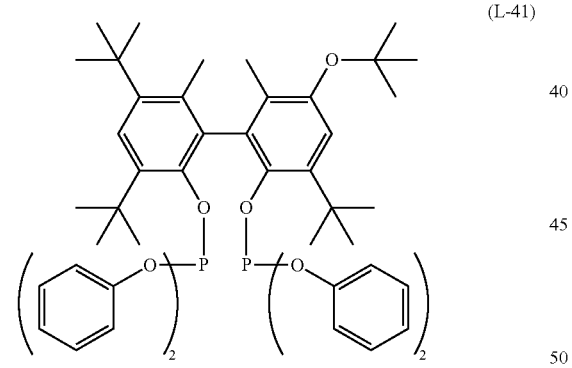
(L-41)
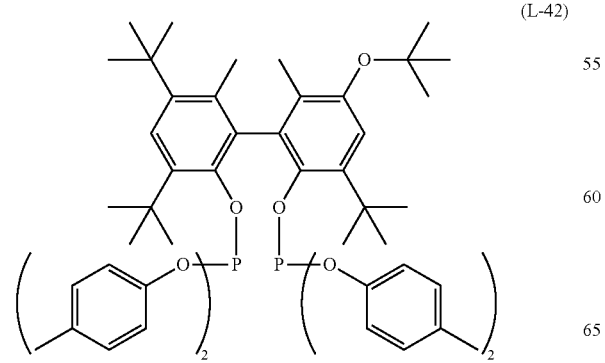
(L-42)
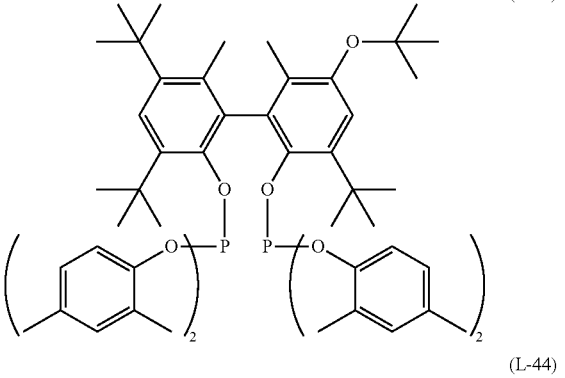
(L-43)
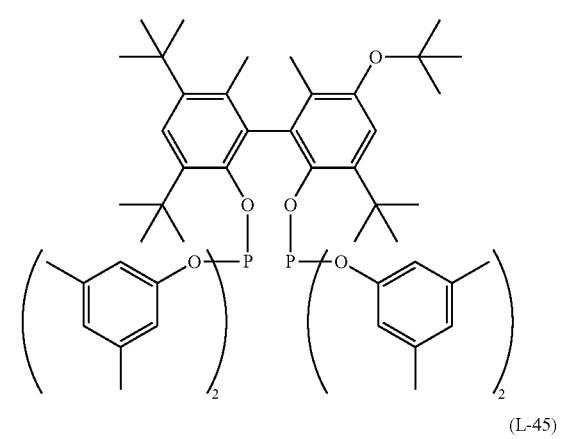
(L-44)
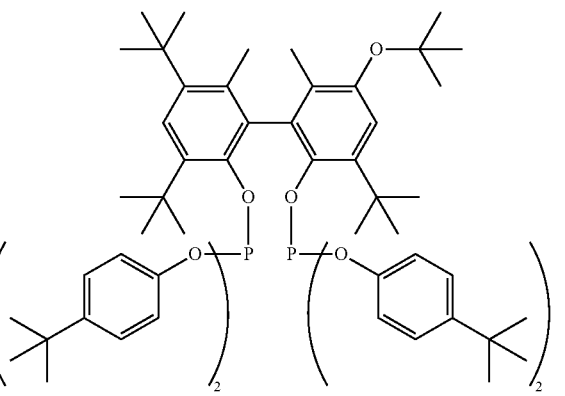
(L-45)
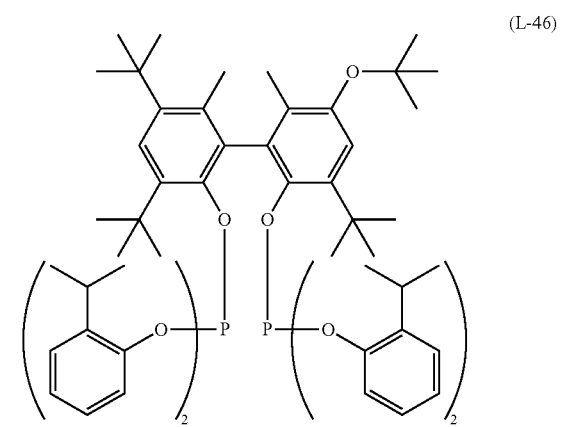
(L-46)

-continued
(L-47)
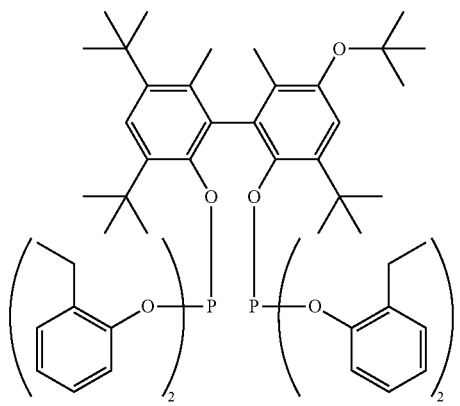
(L-48)
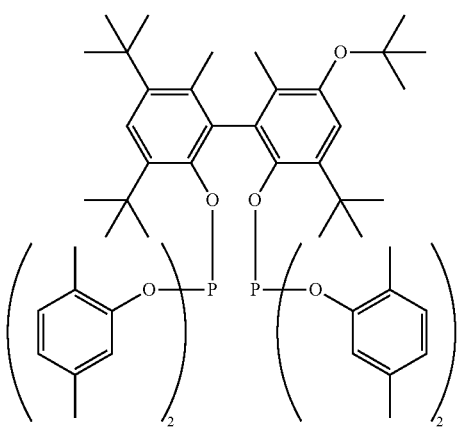
(L-49)
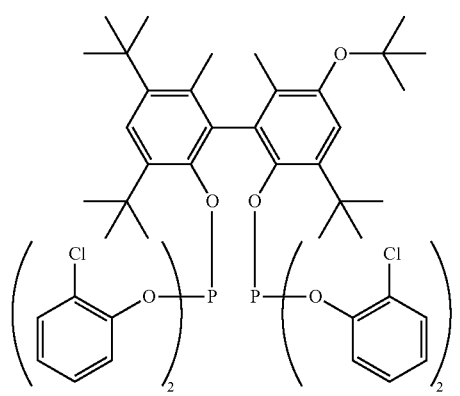
(L-50)
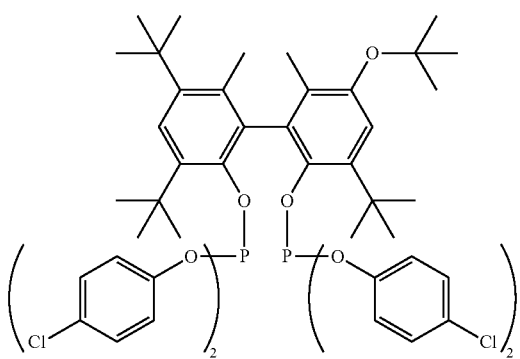
-continued
(L-51)
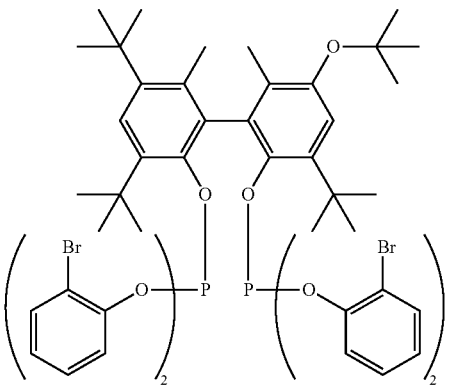
(L-52)
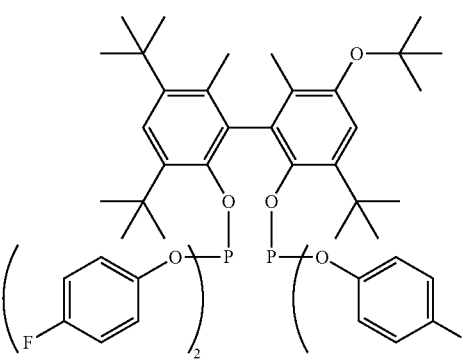
(L-53)
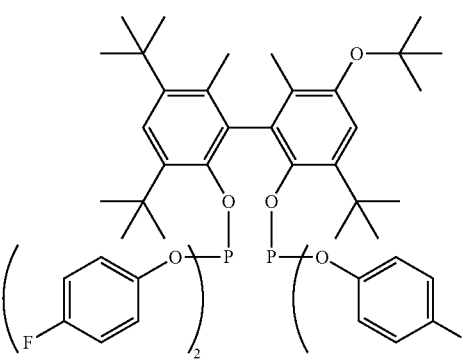
(L-54)
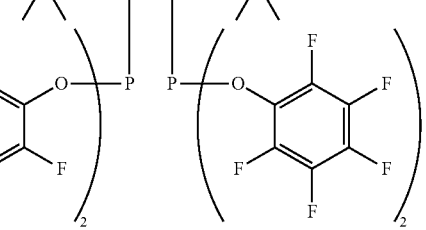

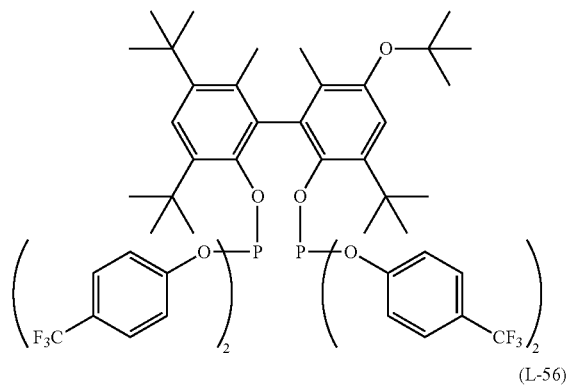
(L-55)
(L-56)
(L-57)
(L-58)
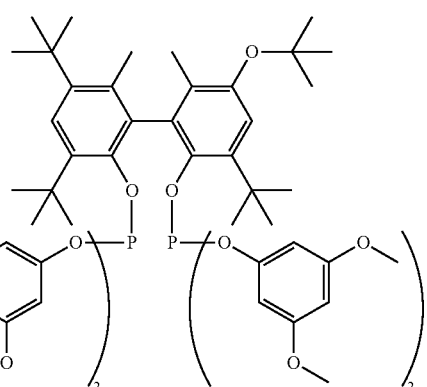
(L-59)
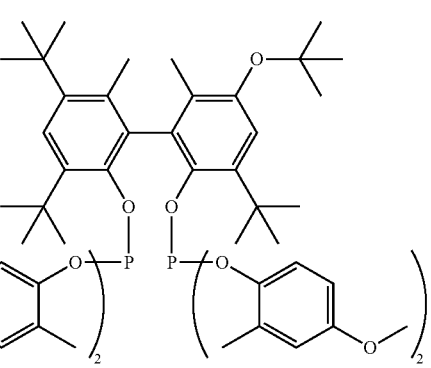
(L-60)
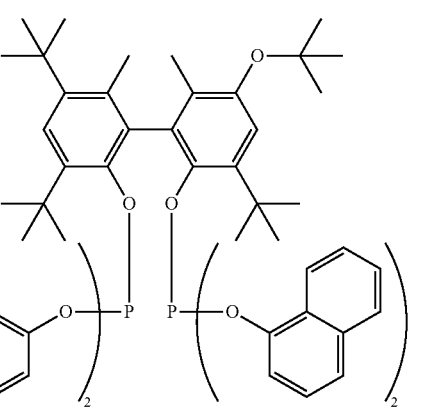
(L-61)
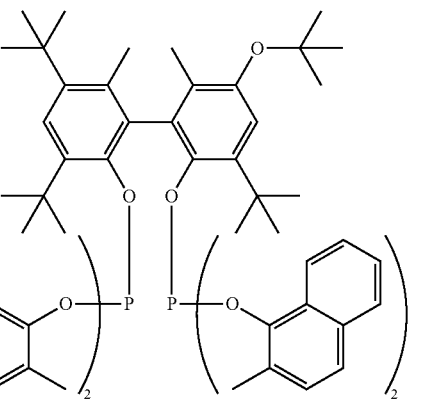
(L-62)

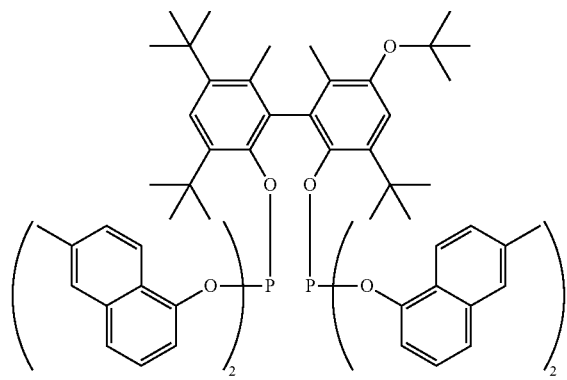
(L-63)
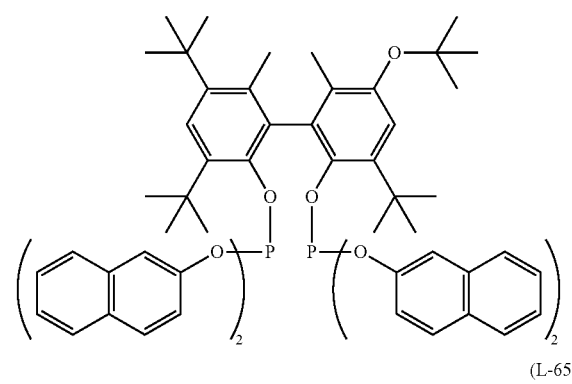
(L-64)
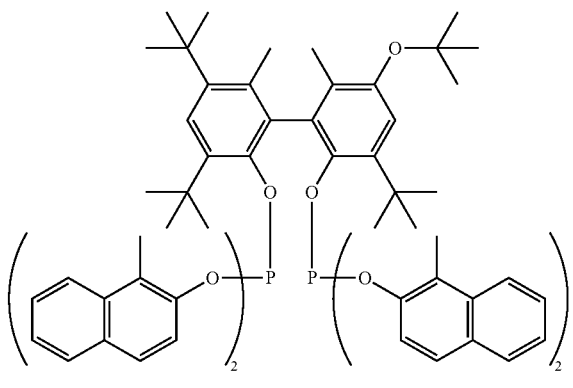
(L-65)
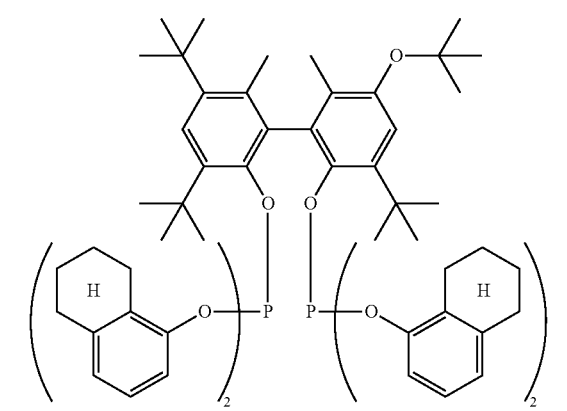
(L-66)
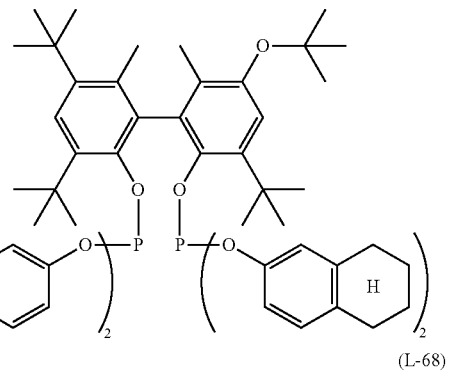
(L-67)
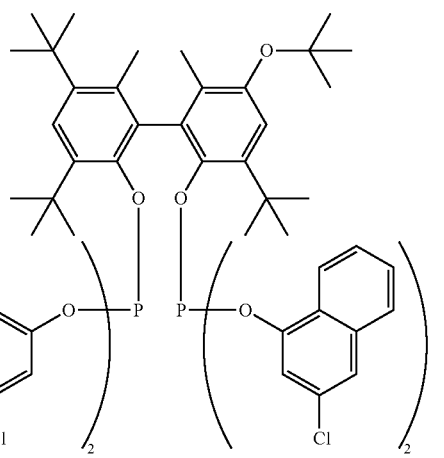
(L-68)
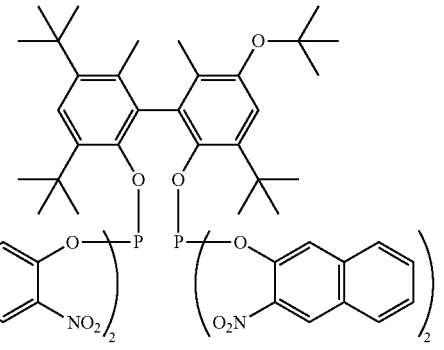
(L-69)
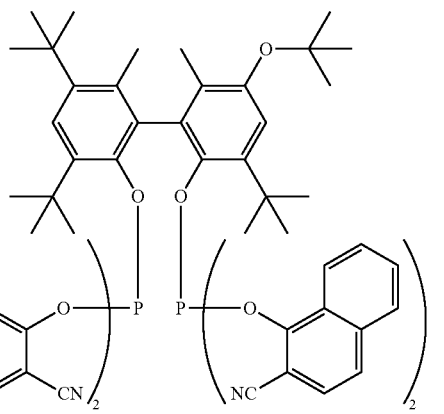
(L-70)

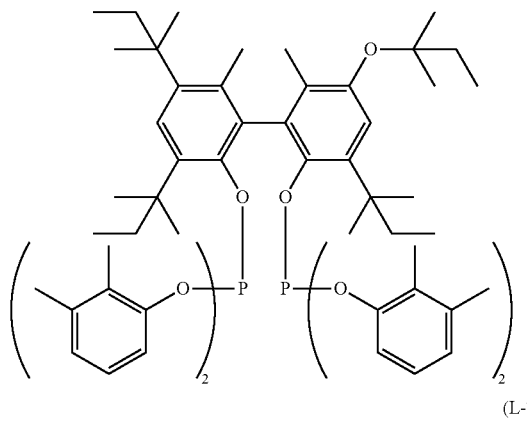
(L-71)
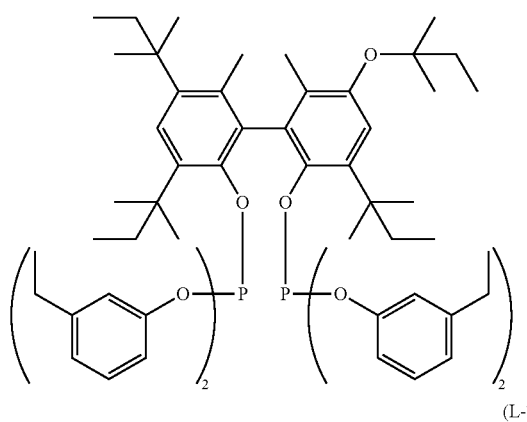
(L-72)
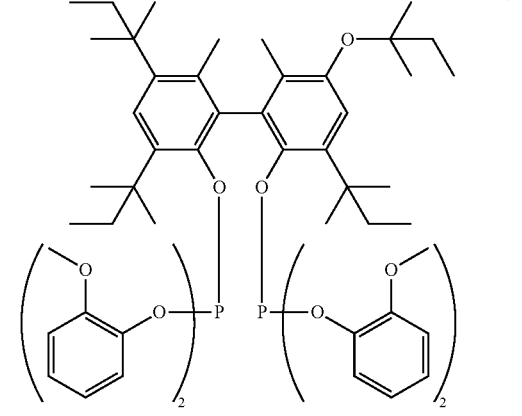
(L-73)
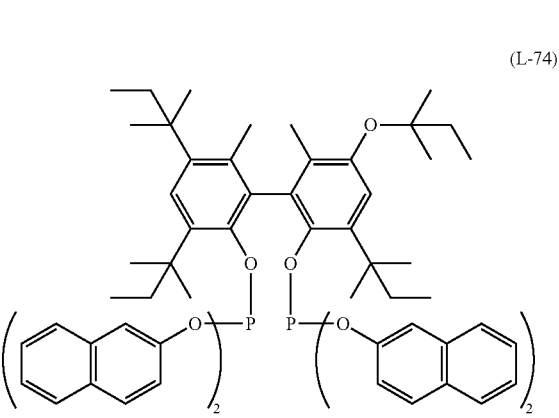
(L-74)
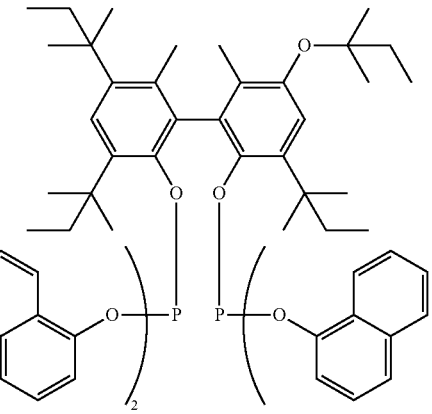
(L-75)
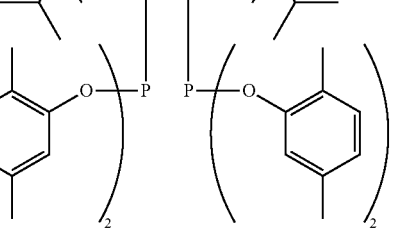
(L-76)
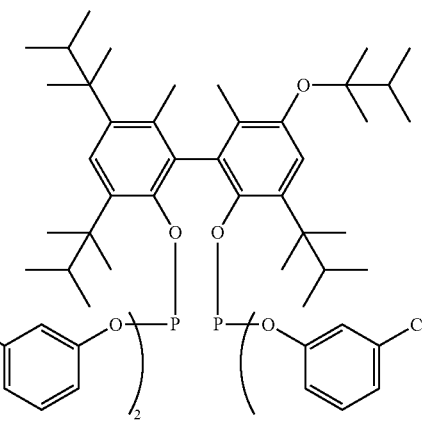
(L-77)

(L-78)

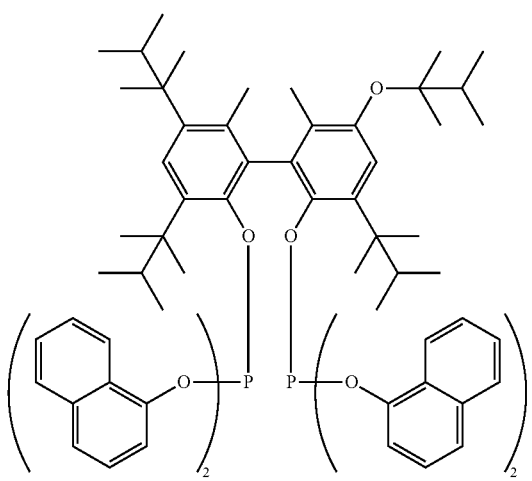

(L-79)

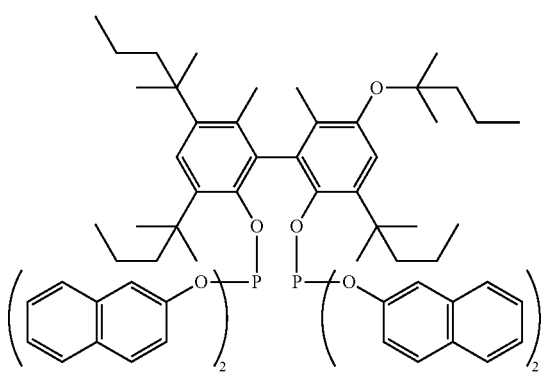

(L-80)

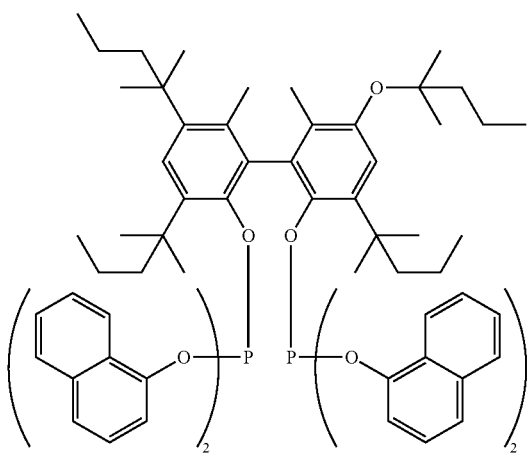

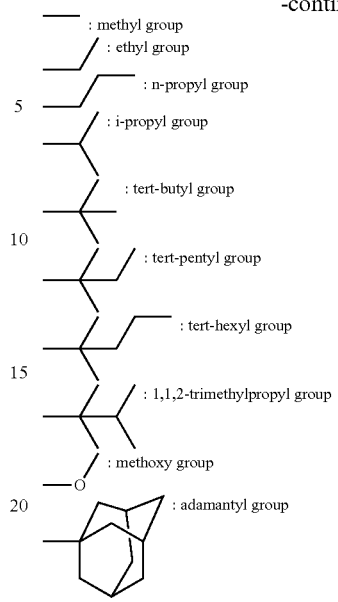

The dihydroxybiphenyl compound represented by formula (1) can be synthesized by applying a Suzuki-Miyaura cross-coupling reaction as in the following reaction formula (A). More specifically, a boronic acid derivative of the corresponding phenol compound and a halide of the corresponding phenol compound are reacted using a palladium catalyst having a phosphine ligand in the presence of a basic compound such as sodium carbonate, and the dihydroxybiphenyl compound can thereby be synthesized.

Reaction formula (A)

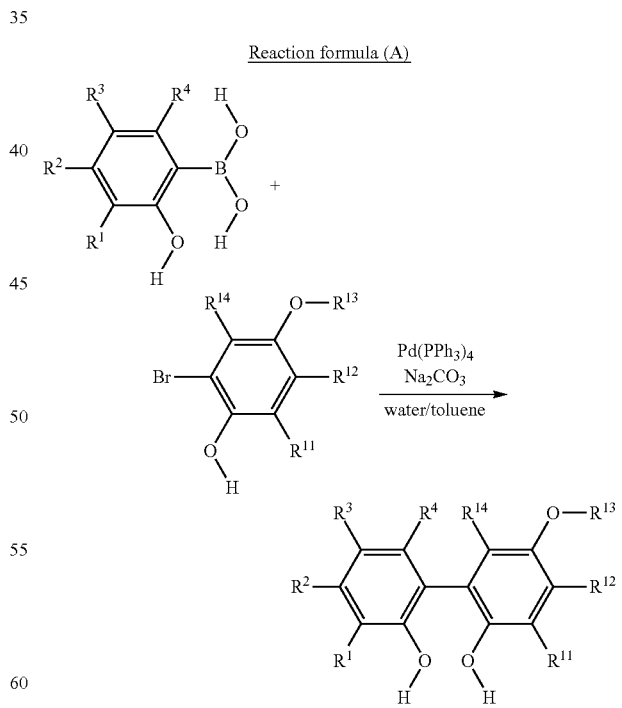

In reaction formula (A), $R^1$ to $R^4$ and $R^{11}$ to $R^{14}$ have the same meanings as $R^1$ to $R^4$ and $R^{11}$ to $R^{14}$ in formula (1), respectively, and B represents a halogen atom.

In addition, a dihydroxybiphenyl compound in which right and left substituents are the same ($R^1$=$R^{11}$, $R^2$=$R^{12}$, $R^3=R^{13}$, $R^4=R^{14}$) can be synthesized by holding the corresponding phenol compound for a long time under heating in the presence of air or at room temperature in the presence of air (reaction formula (B)).

Above all, in the phenol compound in which $R^1$ and $R^3$ are a tert-butyl group, $R^2$ is a hydrogen atom, and $R^4$ is a methyl group, such as 4,6-di-tert-butyl-m-cresol, a reaction of reaction formula (B) is relatively likely to proceed and even in the absence of a catalyst, the compound can be synthesized by heating the system, for example, at a temperature of 50 to 100° C. for about 100 hours in the presence of air. In addition, even at room temperature of about 20° C., the compound can be synthesized by holding the system in the presence of air for several months.

Reaction formula (B)

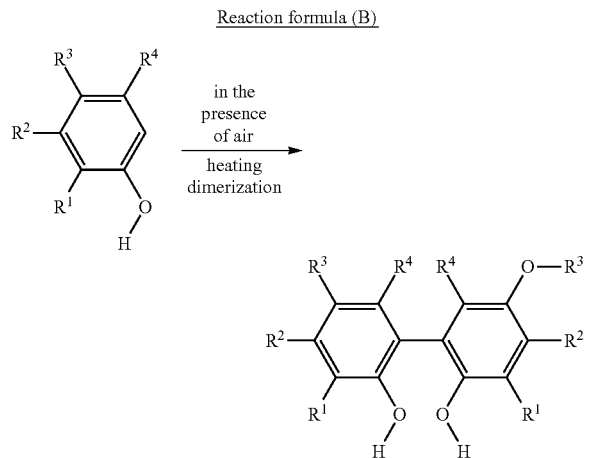

The dihydroxybiphenyl compound represented by formula (1) can also be synthesized by an oxidation coupling reaction using a copper catalyst in the presence of methanol and air.

The bisphosphite compound represented by formula (2) can be synthesized by reacting an alkali metal salt or alkaline earth metal salt of a dihydroxybiphenyl compound having a substituent, represented by the following formula (3) (in formula (3), $R^1$ to $R^4$ and $R^{11}$ to $R^{14}$ have the same meanings as $R^1$ to $R^4$ and $R^{11}$ to $R^{14}$ in formula (2), respectively, and M is an alkali metal or an alkaline earth metal), with a phosphorus compound represented by the following formulae (4) and/or (5) (in the formulae, $Z^1$ to $Z^4$ have the same meanings as $Z^1$ to $Z^4$ in formula (2), respectively) (bidentate phosphite synthesis method 1).

The bisphosphite compound can also be synthesized by reacting an alkali metal salt or alkaline earth metal salt of a dihydroxybiphenyl compound having a substituent, represented by the following formula (3) (in formula (3), $R^1$ to $R^4$ and $R^{11}$ to $R^{14}$ have the same meanings as $R^1$ to $R^4$ and $R^{11}$ to $R^{14}$ in formula (2), respectively, and M is an alkali metal or an alkaline earth metal), with bis(dialkylamino)chlorophosphine represented by the following formula (6) (in the formula, $R^{20}$ represents a linear or branched alkyl group having a carbon number of 1 to 5, such as methyl group, ethyl group, n-propyl group and i-propyl group) to obtain a biphenyldioxy intermediate having two bis(dialkylamino) phosphino groups, obtaining a biphenyldioxy intermediate having two dichlorophosphino groups by the reaction with hydrogen chloride, and further reacting the intermediate with phenols in the presence of a base catalyst (bidentate phosphite synthesis method 2).

The bidentate phosphite synthesis method 1 is described in detail here, and details of the bidentate phosphite synthesis method 2 are described in JP-A-2000-53688.

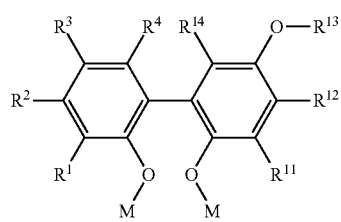

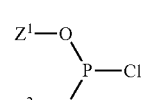

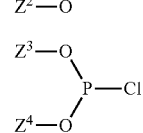

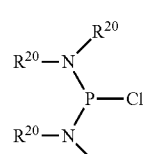

An alkali metal salt or alkaline earth metal salt of a dihydroxybiphenyl compound represented by formula (3) can be synthesized by reacting a dihydroxybiphenyl compound represented by formula (1) (in formula (1), $R^1$ to $R^4$ and $R^{11}$ to $R^{14}$ have the same meanings as $R^1$ to $R^4$ and $R^{11}$ to $R^{14}$ in formula (2), respectively) with an alkali metal compound such as n-BuLi (normal-butyllithium), Na, NaH or KH or with an alkaline earth metal compound such as methylmagnesium bromide or ethylmagnesium bromide, in a solvent preferably under an inert gas atmosphere such as nitrogen.

The amount of the alkali metal compound or alkaline earth metal compound used may be sufficient if it is usually 2 mol per mol of the dihydroxybiphenyl compound represented by formula (1), but the compound may be used in a lager amount, if desired.

As the solvent, ethers such as tetrahydrofuran and diethyl ether, hydrocarbons such as hexane and toluene, a nitrogen-containing compound such as pyridine, triethylamine and N,N,N',N'-tetramethylethylenediamine, and a mixture thereof are suitably used.

The reaction temperature may be appropriately selected from the range from −70° C. to the boiling point of solvent, and a method of performing the reaction at a lower temperature of, for example, from −30° C. to 10° C. at the start of reaction and thereafter, gradually raising the temperature up to the boiling point of the solvent may also be employed.

In view of reaction operation, the reaction is preferably performed using n-BuLi or NaH and using, as the solvent, tetrahydrofuran.

The reaction time may be selected from the range of usually from 1 minute to 48 hours but is preferably on the order of from 10 minutes to 4 hours.

As for the compound represented by formula (3), a reaction solution after synthesizing the compound may be used directly in the next step without any particular purification or may be previously subjected to a treatment such as washing with a poor solvent or isolation by a recrystallization operation.

The phosphorus compound represented by formula (4) or (5) can be synthesized usually by reacting phosphorus trichloride (PCl$_3$) with phenols represented by $Z^1$—OH, $Z^2$—OH, $Z^3$—OH or $Z^4$—OH (in the formulae, $Z^1$ to $Z^4$ have the same meanings as $Z^1$ to $Z^4$ in formula (2)) in the presence or absence of a base, preferably, in an inert gas atmosphere such as nitrogen, in a solvent or without a solvent.

A phosphorus compound in which paired $Z^1$ and $Z^2$ or paired $Z^3$ and $Z^4$ are the same can be easily synthesized and therefore, is preferred. Accordingly, it is more preferred that both of paired $Z^1$ and $Z^2$ and paired $Z^3$ and $Z^4$ are the same, and it is still more preferred that all of $Z^1$ to $Z^4$ are the same.

Examples of the base include a nitrogen-containing base such as pyridine, triethylamine and diethylamine, and an inorganic base such as sodium carbonate and potassium carbonate. Among others, a nitrogen-containing base is preferably used because the reaction operation is easy. The amount of the base used is usually 2 mol per mol of PCl$_3$.

If the amount of the base is too large or too small, the amount of unnecessary byproducts of phosphites, such as P(OZ$^1$)$_2$(OZ$^2$), P(OZ$^1$)(OZ$^2$)$_2$, P(OZ$^1$)$_3$ and P(OZ$^2$)$_3$, or of a dichloro compound, such as Cl$_2$P(OZ$^1$), is disadvantageously increased.

As for the reaction temperature, an arbitrary temperature may be selected, but, for example, in the case of using a nitrogen-containing base as the base, the reaction is preferably performed at a temperature of 0 to 5° C.

As for the reaction time, a range from 1 minute to 48 hours may be selected, but a reaction time of approximately from 5 minutes to 10 hours is preferred.

In the case of performing the reaction in the presence of a base, a salt of hydrogen chloride generated as a byproduct along with the progress of reaction and the base is present usually as a solid in the reaction solution, but the salt can be removed from the reaction system by filtration or other methods preferably in an inert gas atmosphere such as nitrogen. In the case of performing the reaction in the absence of a base, hydrogen chloride generated as a byproduct can be removed from the reaction system by bubbling an inert gas such as nitrogen gas or argon gas in the reaction system.

The phosphorus compound represented by formula (4) or (5) is sometimes obtained as a mixture of the above-described unnecessary phosphites and a dichloro compound, but the process may advance to the next step without separating the compound from these byproducts. The method for separating the phosphorus compound represented by formula (4) or (5) from the byproducts above includes a method by recrystallization using an aliphatic hydrocarbon solvent such as hexane and heptane, distillation, etc.

The bisphosphite compound represented by formula (2) can be synthesized by bringing the compound represented by formula (3) and the compound represented by formula (4) and/or (5) into contact at 20° C. or less for 1 minute or more in a solvent or without a solvent.

The contact is preferably performed in an inert gas atmosphere such nitrogen, and the target bisphosphite compound can be synthesized by a method of mixing the compound represented by formula (3) and the compound represented by formula (4) and/or (5) at a temperature of preferably 0° C. or less, more preferably −30° C. or less, most preferably −50° C. or less, with maintaining the temperature for 1 minute or more, preferably from 3 to 60 minutes, and gradually raising the temperature.

The temperature rise rate may be appropriately selected from the range of 0.1 to 20° C./min, and a rate of 0.5 to 10° C./min is preferred.

As the solvent, ethers such as tetrahydrofuran, diethyl ether and dioxane, hydrocarbons such as hexane and toluene, nitrogen-containing compounds such as pyridine, triethylamine and N,N,N',N'-tetramethylethylenediamine, and a mixture thereof may be used.

As for the amount of the solvent, the solvent is preferably used in a minimum amount necessary to dissolve the target material produced but may be used in a larger amount.

The method for purifying the bisphosphite compound represented by formula (2) includes, for example, a method by column development (chromatography), a method by suspension washing (suspending and washing), and a method by recrystallization.

The method by column development includes a method using silica gel, alumina, etc. as the packing material. In addition, the developing solution includes ethers such as tetrahydrofuran and dioxane, aliphatic hydrocarbons such as hexane and heptane, aromatic hydrocarbons such as toluene and xylene, esters such as ethyl acetate and methyl acetate, and halogenated hydrocarbons such as chloroform and dichloroform, and such a developing solution is mixed with a single solvent or two or more kinds of solvents so as to suit the purification of the target material and used.

In the method by suspension washing, the target material can be purified by a method where after the completion of the bisphosphite synthesis reaction, metal chlorides (MCl) generated as a byproduct are removed from the reaction solution by filtration or with a polar solvent such as water, the solution is then evaporated to dryness, the residue is stirred in a solvent, for example, acetonitrile, aliphatic hydrocarbons such as hexane and heptane, ketones such as acetone and diethyl ketone, and alcohols such as methanol and ethanol, and unwanted materials are thereby dissolved in the solvent without dissolving the target in the solvent.

The method by recrystallization includes, for example, a method where after the completion of the bisphosphite synthesis reaction, metal chlorides generated as a byproduct are removed from the reaction solution by filtration or with a polar solvent such as water, the solution is then evaporated to dryness, solids are precipitated, for example, by a method of dissolving the residue in a smallest amount of solvent capable of dissolving the residue, and cooling the solution; or a method of dissolving the residue in a smallest amount of solvent capable of dissolving the residue, adding a solvent in which the bisphosphite compound as a target material is insoluble or sparingly soluble, and, if desired, cooling the solution, and the solid is separated by filtration or other methods and further washed with a solvent incapable of dissolving the solid.

The solvent in which the bisphosphite compound is soluble includes aromatic hydrocarbons such as benzene, toluene and xylene, and ethers such as tetrahydrofuran and dioxane, and the solvent in which the bisphosphite compound is insoluble or sparingly soluble includes, in addition to acetonitrile, aliphatic hydrocarbons such as hexane and heptane, ketones such as acetone and diethyl ketone, and alcohols such as methanol and ethanol.

In the present invention, a hydroformylation reaction is performed using the above-described novel bisphosphite compound, so that a high reaction rate and excellent selectivity for the target product can be satisfied at the same time.

In this connection, a composition containing the bisphosphite compound of the present invention, such as a mixture of the novel bisphosphite compound of the present invention and other bisphosphite compound, is included in the embodiment of the present invention. In the case of a mixture, the mixing ratio is not limited. The mixture includes, for example, a mixture of the bisphosphite compound of the present invention and a symmetric bisphosphite compound used in Comparative Example 1, wherein the mixing ratio (by weight) is former/latter=from 0.01/99.99 to 99.99/0.01.

[Production Method of Aldehydes or Alcohol]

The production method of aldehydes of the present invention is characterized by reacting an olefin compound with carbon monoxide and hydrogen in the presence of a compound of a metal of Groups 8 to 10 and the bisphosphite compound of the present invention The olefin compound is not particularly limited as long as it is an organic compound having at least one olefinic double bond in its molecule. Specifically, examples thereof include ethylene, propylene, butene, butadiene, pentene, hexene, hexadiene, octene, octadiene, decene, hexadecene, octadecene, icosene, docosene, styrene, α-methylstyrene, cyclohexene, a lower olefin mixture such as mixture of propylene and butene, mixture of 1-butene, 2-butene and isobutylene, and mixture of 1-butene, 2-butene, isobutylene and butadiene, an olefin oligomer isomer mixture like a dimer, trimer and tetramer of a lower olefin such as propylene, n-butene and isobutylene, and polar group-substituted olefins such as acrylonitrile, allyl alcohol, 1-hydroxy-2,7-octadiene, 3-hydroxy-1,7-octadiene, oleyl alcohol, 1-methoxy-2,7-octadiene, methyl acrylate, methyl methacrylate and methyl oleate.

A hydroformylation reaction is conducted using the olefin compound above, and corresponding aldehydes can thereby be produced. Usually, the production ratio (L form/B form) between linear form (L form) and branched form (B form) of the obtained aldehydes is preferably 1 or more, more preferably 5 or more, and still more preferably 10 or more.

In the production method of aldehydes of the present invention, as for the compound of a metal of Groups 8 to 10 used as a catalyst or the precursor thereof, a hydride, halide, organic acid salt, inorganic acid salt, oxide, carbonyl compound, amine compound, olefin-coordinated compound, phosphine-coordinated compound or phosphite-coordinated compound of a metal of Groups 8 to 10 can be used, and examples thereof include, but are not necessarily limited to, a ruthenium compound such as ruthenium trichloride, dichloro(p-cymene)ruthenium dimer and dichlorotris(triphenylphosphine)ruthenium, a palladium compound such as palladium acetate and palladium chloride, an osmium compound such as osmium trichloride, an iridium compound such as iridium trichloride and iridium carbonyl, a platinum compound such as platinic acid, sodium hexachloroplatinate and potassium platinate, and a cobalt compound such as dicobalt octacarbonyl and cobalt stearate, and a rhodium compound such as rhodium trichloride, rhodium nitrate, rhodium acetate, $Rh(acac)(CO)_2$, $[Rh(OAc)(cod)]_2$, $Rh_4(CO)_{12}$, $Rh_6(CO)_{16}$, $HRh(CO)(PPh_3)_3$, $[Rh(OAc)(CO)_2]_2$, $[Rh(\mu\text{-}S(t\text{-}Bu))(CO)_2]_2$ and $[RhCl(cod)]_2$, (in the present description, acac stands for an acetylacetonate group, OAc stands for an acetyl group, cod stands for 1,5-cyclooctadiene, Ph stands for a phenyl group, and t-Bu stands for a tert-butyl group). Among these, a cobalt, rhodium or ruthenium compound is preferred, and a rhodium compound is particularly preferred.

A complex of the bisphosphite compound with the above-described metal of Groups 8 to 10 is previously formed, and the production method of aldehydes of the present invention can be conducted in the presence of a catalyst containing the complex. The bisphosphite compound-containing complex of a metal of Groups 8 to 10 can be easily prepared by a known complexation method from a compound of a metal of Groups 8 to 10 and the bisphosphite compound.

In addition, depending on the case, a complex may be formed and used in a hydroformylation reaction zone by supplying a compound of a metal of Groups 8 to 10 and the bisphosphite compound thereto.

In the case where a complex of the bisphosphite compound with the metal of Groups 8 to 10 is previously formed and the production method of aldehydes of the present invention is conducted in the presence of a catalyst containing the complex, the molar ratio of the bisphosphite compound to the metal of Groups 8 to 10 is preferably from 0.00004 to 500, more preferably from 0.0002 to 100, and still more preferably from 0.001 to 50.

In the production method of aldehydes of the present invention, the amount of the complex used is not particularly limited and although there is a limit to be taken into account in view of catalytic activity, economic efficiency, etc., the complex may be supplied to the reaction zone such that the concentration of the metal of Groups 8 to 10 in the reaction solution in the hydroformylation reaction zone becomes, in terms of metal atoms, from 0.05 to 5,000 mg/L, preferably from 0.5 to 1,000 mg/L, more preferably from 5 to 500 mg/L.

If the concentration of the metal of Groups 8 to 10 serving as a catalyst is too low, sufficient reactivity may not be exhibited, and if the concentration of the metal of Groups 8 to 10 is too high, the catalyst cost may rise excessively. If the amount of the bisphosphite compound used is too small, sufficient reactivity may not be obtained, and if it is too large, the cost of the bisphosphite compound may rise excessively.

In the case of forming and using a complex in a hydroformylation reaction zone by supplying a compound of a metal of Groups 8 to 10 and the bisphosphite compound thereto, similarly, the amount used of the compound of a metal of Groups 8 to 10 is not particularly limited and although there is a limit to be taken into account in view of catalytic activity, economic efficiency, etc., in the present invention, the concentration of the compound of a metal of Groups 8 to 10 in the reaction solution in the hydroformylation reaction zone is usually, in terms of metal atoms, from 0.05 to 5,000 mg/L, preferably from 0.5 to 1,000 mg/L, and more preferably from 5 to 500 mg/L.

If the concentration of the metal of Groups 8 to 10 serving as a catalyst is too low, sufficient reactivity may not be exhibited, and if the concentration of the metal of Groups 8 to 10 is too high, the catalyst cost may rise excessively.

The amount of the bisphosphite compound used is not particularly limited and is appropriately set so that desirable results can be obtained in terms of catalytic activity and selectivity. Usually, the amount used is from 0.00004 to 500 mol, preferably from 0.0002 to 100 mol, more preferably from 0.001 to 50 mol, and most preferably from 0.01 to 30 mol, per mol of the metal of Groups 8 to 10. If the amount of the bisphosphite compound used is too small, sufficient reactivity may not be obtained, and if it is too large, the cost of the bisphosphite compound may rise excessively.

In the production method of aldehydes of the present invention, use of a reaction solvent is not essential but, if desired, a solvent inert to the hydroformylation reaction can be caused to be present.

Specific examples of preferable solvents include aromatic hydrocarbons such as toluene, xylene and dodecylbenzene, ketones such as acetone, diethyl ketone and methyl ethyl ketone, ethers such as tetrahydrofuran and dioxane, esters such as ethyl acetate and di-n-octyl phthalate, a high-boiling-point component generated as byproducts at the time of hydroformylation reaction, such as aldehyde condensate, and an olefin compound as a reaction raw material.

The reaction conditions for performing the production method of aldehydes of the present invention are the same as those that have conventionally been commonly employed. The reaction temperature is usually selected from the range of from 15 to 200° C., preferably from 50 to 150° C., and the carbon monoxide partial pressure and hydrogen partial pressure are usually selected from the range of from 0.0001 to 20 MPaG, preferably from 0.01 to 10 MPaG, and particularly preferably from 0.1 to 5 MPaG.

The molar ratio ($H_2$/CO) of carbon monoxide and hydrogen is usually selected from the range of from 10/1 to 1/10, and preferably from 3/1 to 1/3.

As for the reaction system, the reaction may be performed in either a continuous system or a batch system, in a stirring-type reactor or a bubbling column-type reactor.

The reaction time is not particularly limited as long as the time is basically long enough to sufficiently achieve the intended production of aldehydes, and the reaction time can be appropriately selected based on the catalyst concentration, reaction conditions, reactor size and other conditions. The reaction time is generally from 1 minute to 100 hours, preferably from 5 minutes to 20 hours, more preferably from 20 minutes to 10 hours.

In the production method of aldehydes of the present invention, after the produced aldehydes are separated by distillation or other methods, a hydroformylation reaction of an olefin compound can again be performed using the recovered solution containing the metal of Groups 8 to 10 and the bisphosphite compound.

Furthermore, at the time of continuously converting an olefin compound into aldehydes, the reaction solution remaining after separating a part or whole of the aldehydes produced may also be continuously circulated as a catalyst solution to the hydroformylation reaction tank.

In addition, an alcohol can be produced by allowing the obtained aldehydes to be directly used for a reaction with hydrogen, i.e., a hydrogenation reaction, or to be dimerized and then used for a hydrogenation reaction. For the hydrogenation reaction, a known solid catalyst in which a metal such as Ni, Cr and Cu is supported on a support may be used. The reaction conditions are usually a temperature of 60 to 200° C. and a hydrogen pressure of approximately from 0.1 to 20 MPaG.

EXAMPLES

Example 1

Production of Dihydroxybiphenyl Compound of the Present Invention (Compound A)

About 500 g of 4,6-di-tert-butyl-m-cresol (DBMC) was put in a glass vessel and heated at 80° C. for 96 hours in the presence of air. Subsequently, the obtained solution (Sample 1) was analyzed by gas chromatography and found to allow for residual presence of 85.7 wt % of DBMC and contain 3.5 wt % of 2-tert-butyl-5-methyl-1,4-benzoquinone (BMBQ) and 1.7 wt % of Compound A assumed to have the following formula. Next, the following operation was performed using Sample 1 to isolate Compound A, and the structure of Compound A was identified.

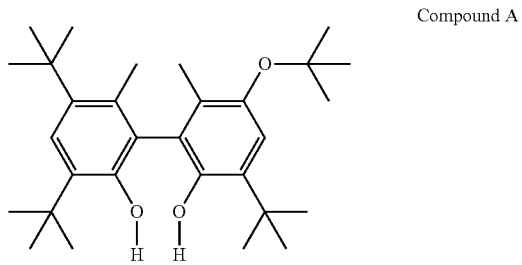 [SMILES: Cc1c(OC(C)(C)C)cc(C(C)(C)C)c(O)c1-c1c(C)c(C(C)(C)C)cc(C(C)(C)C)c1O]

Compound A

<Isolation of Compound A>

About 500 g of Sample 1 was charged into a glass-made simple distillation apparatus and heated in an oil bath at about 120° C. under reduced pressure of 3 mmHg to distill off BMBQ and DBMC, as a result, 38.0 g of a red-brown highly viscous oil was obtained. This oil was analyzed by gas chromatography and found to contain 32.9 wt % of DBMC and 22.4 wt % of Compound A.

Subsequently, 19 g of acetone was added to the oil, stirred at room temperature to dissolve DBMC, and filtered to obtain 6.0 g of a yellow-white solid. Furthermore, 4 ml of hexane was added and after the solid was suspension-washed under heating in an oil bath at 70° C., the solution was filtered to obtain 3.4 g of a yellow-white solid. The solid was analyzed by gas chromatography and found to contain 83.0 wt % of Compound A.

<Structure Identification of Compound A>

From the sample in a different lot containing Compound A, about 6.7 mg of Compound A was isolated by liquid chromatography analysis (LC analysis) and subjected to measurements of mass spectrum (MS) and various NMRs ($^1$H-NMR, HH-COSY, HMQC, HMBC). The analytical values of Compound A were as follows.

(MS (ESI Method) Analysis Results)

The molecular weight was judged to be 454 by observing 454 ([M]$^+$) in positive mode and 453 ([M–H]$^-$) in negative mode. In addition, the composition formula was estimated to be $C_{30}H_{46}O_3$ from the results of accurate mass measurement.

($^1$H-NMR (CDCl$_3$, TMS))

δ1.36 (9H, s, signal of 7), δ1.39 (9H, s, signal of 9), δ1.40 (9H, s, signal of 4), δ1.42 (9H, s, signal of 2), δ1.78 (3H, s, signal of 6), δ2.01 (3H, s, signal of 1), δ4.76 (1H, s, signal of 5), δ4.79 (1H, s, signal of 10), δ7.04 (1H, s, signal of 8), δ7.39 (1H, s, signal of 3).

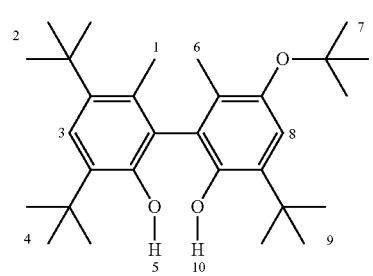 [SMILES: Cc1c(OC(C)(C)C)cc(C(C)(C)C)c(O)c1-c1c(C)c(C(C)(C)C)cc(C(C)(C)C)c1O]

Figure for Identification of $^1$H-NMR Signals
($^{13}$C-NMR (CDCl$_3$, TMS))

δ14.09 (signal of c), δ18.56 (signal of C), δ29.09 (signal of a), δ29.55 (signal of b), δ29.59 (signal of B), δ31.50 (signal of A), δ34.61 (signal of d), δ34.98 (signal of D), δ35.83 (signal of F), δ78.91 (signal of f), δ122.07 (signal of i), δ122.33 (signal of I), δ123.02 (signal of e), δ125.47 (signal of E), δ129.89 (signal of h), δ132.42 (signal of K), δ133.79 (signal of H), δ134.03 (signal of k), δ139.96 (signal of G), δ147.19 (signal of g), δ148.01 (signal of j), δ149.80 (signal of J).

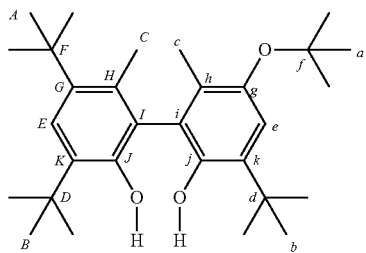

Figure for Identification of $^{13}$C-NMR Signals
(Summary of Measurement Results of HMQC and HMBC Spectra)

TABLE 1

|  |  | Correlations Observed in HMQC | Correlations Observed in HMBC |
|---|---|---|---|
| $^1$H-NMR Signal | 7 | a | a, f |
|  | 9 | b | d, k |
|  | 4 | B | D, K |
|  | 2 | A | F, G |
|  | 6 | c | g, h, i |
|  | 1 | C | G, H, J |
|  | 5 | — | J, K |
|  | 10 | — | j, k |
|  | 8 | e | d, h, j |
|  | 3 | E | F, H, J |

From these results, the structure of Compound A was identified as in the following formula (7).

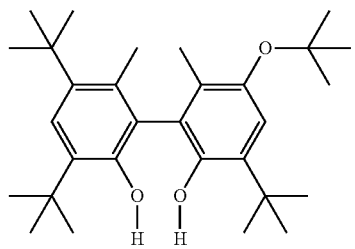

(7)

Example 2

Production of Bisphosphite Compound of the Present Invention

A toluene (24 ml) solution of 1-naphthol (3.39 g, 23.51 mmol) and pyridine (2.07 g, 26.11 mmol) was added dropwise to a toluene (20 ml) solution of phosphorus trichloride (1.42 g, 10.38 mmol) in a nitrogen atmosphere at 0° C. over 1 hour with stirring. Subsequently, solid pyridine hydrochloride generated as a byproduct was separated by filtration, and the solvent was distilled off under reduced pressure to obtain an oily substance containing ClP(O-1-naphthyl)$_2$.

On the other hand, n-butyllithium (concentration: 1.6 mol/L, 6.60 ml, 10.56 mmol) dissolved in hexane was added dropwise to a tetrahydrofuran (20 ml) solution of a solid (2.36 g, 1.96 g in terms of Compound A, 4.31 mmol) containing Compound A obtained in Example 1, in a nitrogen atmosphere at 0° C. and then boiled under reflux for 50 minutes to obtain a dilithio form of Compound A.

Subsequently, 20 ml of tetrahydrofuran was added to and dissolved in the oily substance containing ClP(O-1-naphthyl)$_2$ obtained above and cooled to −78° C. by using a dry ice/ethanol bath, and the tetrahydrofuran solution containing a dilithio form of Compound A was added dropwise over 1 hour with stirring. After the dropwise addition, the temperature was slowly elevated to room temperature over 1 hour, and the solvent was distilled off under reduced pressure by means of an evaporator to obtain a pale yellow oily substance.

Furthermore, 100 ml of toluene was added to and dissolved in the pale yellow oily substance, and the solution was washed three times with 100 ml of pure water to water-wash and remove LiCl. The toluene phase was dried using magnesium sulfate and after separating the magnesium sulfate by filtration, the obtained dry toluene phase was concentrated by an evaporator to obtain 1.68 g of a yellow-white powder.

A solution containing only the bisphosphite compound was fractionated by silica gel column chromatography (developing solution: toluene/hexane=1/3), and the solvent was distilled off in vacuum to obtain 0.98 g of a white powder solid (yield: 20.8%, LC purity: 99.9%). The analytical values of this compound were as follows.

($^{31}$P-NMR (CDCl$_3$, phosphoric acid))
δ133.0 (d, J=16.5 Hz), δ133.5 (d, J=16.5 Hz).
($^{13}$C-NMR (CDCl$_3$, TMS))
δ15.27 (d, J=5.5 Hz), δ19.56 (d, J=4.8 Hz), δ29.21, δ30.69, δ30.88, δ31.08, δ34.99, δ35.43, δ35.91, δ79.05, δ112.50, δ112.69, δ113.53, δ113.70, δ114.50, δ114.63, δ114.94, δ115.07, δ122.41, δ122.46, δ122.52, δ122.57, δ122.72, δ122.79, δ122.97, δ123.18, δ123.22, δ125.24, δ125.26, δ125.37, δ125.40, δ125.42, δ125.48, δ125.49, δ126.08, δ126.12, δ126.19, δ126.20, δ126.37, δ126.66 (d, J=1.4 Hz), δ127.04 (d, J=1.3 Hz), δ127.11 (d, J=1.8 Hz), δ127.19, δ127.23 (d, J=1.8 Hz), δ127.26, δ127.29, δ127.35, δ130.97 (m), δ131.62 (m), δ131.94 (d, J=3.8 Hz), δ134.60, δ134.63, δ134.66, δ135.86 (d, J=3.5 Hz), δ138.12, δ139.82, δ143.67, δ146.46 (m), δ147.94 (d, J=1.8 Hz), δ147.99 (d, J=3.3 Hz), δ148.18 (d, J=5.9 Hz), δ148.32 (d, J=5.3 Hz), δ148.69 (m), δ150.49.
($^1$H-NMR (CDCl$_3$, TMS))
δ1.16 (9H, s), δ1.30 (9H, s), δ1.34 (9H, s), δ1.44 (9H, s), δ1.72 (3H, s), δ1.87 (3H, s), δ6.89 (1H, d, J=7.7 Hz), δ6.93 (1H, d, J=7.7 Hz), δ7.10 to 7.23 (10H, m), δ7.27 to 7.52 (10H, m), δ7.66 to 7.75 (6H, m), δ7.86 (1H, d, J=8.4 Hz), δ7.98 (1H, d, J=8.4 Hz).
(IR (KBr, cm$^{-1}$))
568 (w), 769 (s), 795 (s), 892 (s), 1015 (m), 1041 (m), 1080 (m), 1142 (m), 1172 (m), 1227 (m), 1260 (m), 1363 (m), 1391 (s), 1444 (w), 1461 (m), 1506 (w), 1575 (w), 1595 (w), 2864 (w), 2959 (m), 3051 (w).
(MS (ESI method) m/z 1087.5 ([M+H]$^+$))

The molecular weight was judged to be 1086.5 by observing 1087.5 ([M+H]$^+$) in positive mode. Furthermore, the results of accurate mass measurement were in good agreement with the theoretical values with an error of −0.8 mmDa or −0.7 ppm and therefore, the composition formula was estimated to be $C_{70}H_{72}O_7P_2$.

From these results, the bisphosphite compound having a structure represented by the following formula (8) was identified.

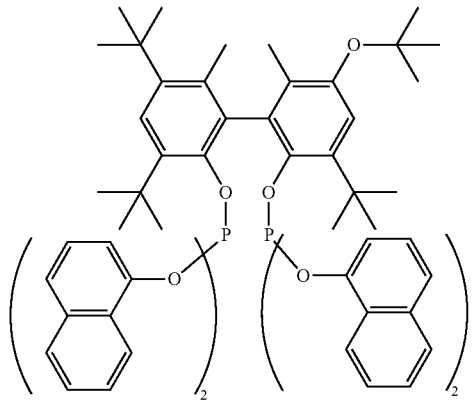

(8)

Example 3

Production of Aldehyde in the Presence of the Bisphosphite Compound of the Present Invention The inside of a thoroughly dried stainless steel-made induction stirring-type autoclave having an inner volume of 50 ml was replaced with nitrogen three times. In a nitrogen atmosphere, 4.2 mg (0.0155 mmol as Rh) of [Rh(OAc)(cod)]$_2$ and 70.3 mg (0.0647 mmol, the ratio of ligand to Rh=4.16) of the bisphosphite compound produced in Example 2 were added to a separately prepared glass-made vessel and after 12.0 ml (10.252 g) of toluene as a solvent and 1.0 ml (0.718 g) of n-dodecane as an internal standard substance for gas chromatography analysis were further added, the mixture was stirred to prepare a catalyst solution.

The catalyst solution was injected into the autoclave by nitrogen pressure, and the autoclave was sealed. The concentration in the reaction solution was 123 mg/L in terms of Rh concentration. The inside of the autoclave was replaced with 2.0 MPaG of nitrogen gas three times, and the nitrogen gas was then released. Subsequently, 1.26 g of propylene was pressure-injected thereinto, and the temperature was elevated to 70° C. Thereafter, an oxo gas (H$_2$/CO=1/1, 0.8 MPaG in terms of the oxo gas partial pressure at the initial stage of reaction) was pressure-injected such that the total pressure inside the autoclave becomes 1.20 MPaG inclusive of the pressure of propylene itself, and the reaction was started. The reaction was continued for 1.5 hours with supplementing the oxo gas consumed during reaction via a secondary pressure regulator from a pressure accumulator to continually maintain the total pressure inside the reactor at 1.20 MPaG.

After the completion of reaction, the reactor was cooled to room temperature, and the gas phase and the liquid phase within the autoclave were collected and subjected to component analysis by gas chromatography. The reaction rate constant (k) was 2.9 h$^{-1}$, the total yield of n-butyl aldehyde and i-butyl aldehyde was 99.4%, and the ratio between n-butyl aldehyde and i-butyl aldehyde (n/i) was 72.3.

Comparative Example 1

Production of Aldehyde in the Presence of Symmetric Bisphosphite Compound

The aldehyde was produced in the same manner except that in Example 3, 70.3 mg of the bisphosphite compound was changed to 69.1 mg (0.0645 mmol, the ratio of ligand to Rh=4.15) of the symmetric bisphosphite compound (the following formula (9)) produced by the method described in Example 11 of Japanese Patent No. 3,812,046.

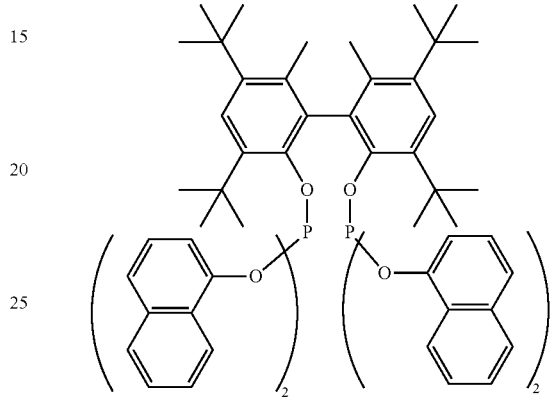

(9)

As a result of synthesis performed in the same manner as in Example 3, the reaction rate constant (k) was 2.7 h$^{-1}$, the total yield of n-butyl aldehyde and i-butyl aldehyde was 99.6%, and the ratio between n-butyl aldehyde and i-butyl aldehyde (n/i) was 66.2.

In this way, it is understood that when the novel bisphosphite compound of the present invention is used as one component of the catalyst in a hydroformylation reaction, the selectivity for the target product is remarkably high.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-160759) filed on Aug. 24, 2017, the contents of which are incorporated herein by way of reference.

The invention claimed is:

1. A bisphosphite compound represented by the following formula (2):

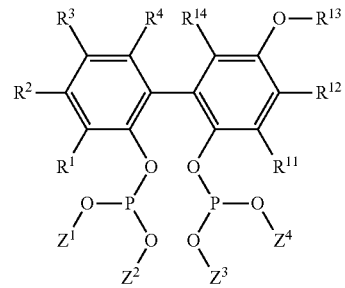

wherein in formula (2), each of R$^1$ and R$^{11}$ independently represents a member selected from the group consisting of a hydrogen atom, an alkyl group having from 1 to 20 carbon atoms, and a cycloalkyl group having from 3 to 20 carbon atoms;

each of $R^2$ and $R^{12}$ independently represents a member selected from the group consisting of a hydrogen atom, an alkyl group having from 1 to 20 carbon atoms, an alkoxy group having from 1 to 20 carbon atoms, a cycloalkyl group having from 3 to 20 carbon atoms, a cycloalkoxy group having from 3 to 20 carbon atoms, a dialkylamino group having from 2 to 20 carbon atoms, an aryl group having from 6 to 20 carbon atoms, an aryloxy group having from 6 to 20 carbon atoms, an alkylaryl group having from 7 to 20 carbon atoms, an alkylaryloxy group having from 7 to 20 carbon atoms, an arylalkyl group having from 7 to 20 carbon atoms, an arylalkoxy group having from 7 to 20 carbon atoms, a cyano group, a hydroxy group, and a halogen atom;

each of $R^3$ and $R^{13}$ independently represents a member selected from the group consisting of a hydrogen atom, an alkyl group having from 1 to 20 carbon atoms, a cycloalkyl group having from 3 to 20 carbon atoms, an aryl group having from 6 to 20 carbon atoms, an alkylaryl group having from 7 to 20 carbon atoms, and an arylalkyl group having from 7 to 20 carbon atoms;

each of $R^4$ and $R^{14}$ independently represents a member selected from the group consisting of a hydrogen atom, an alkyl group having from 1 to 12 carbon atoms, a cycloalkyl group having from 3 to 12 carbon atoms, an alkoxy group having from 1 to 12 carbon atoms, a silyl group, a siloxy group, and a halogen atom; and each of $Z^1$ to $Z^4$ independently represents an aryl group having from 6 to 20 carbon atoms and may have a substituent, and both of paired $Z^1$ and $Z^2$ and paired $Z^3$ and $Z^4$ are not combined.

2. The bisphosphite compound according to claim 1, wherein each of $R^1$ and $R^{11}$ independently represents a tertiary alkyl group having from 4 to 20 carbon atoms, $R^2$ and $R^{12}$ represent a hydrogen atom, each of $R^3$ and $R^{13}$ independently represents a tertiary alkyl group having from 4 to 20 carbon atoms, each of $R^4$ and $R^{14}$ independently represents a member selected from the group consisting of an alkyl group having from 1 to 3 carbon atoms, an alkoxy group having from 1 to 3 carbon atoms, and a halogen atom.

3. The bisphosphite compound according to claim 2, wherein each of $Z^1$ to $Z^4$ independently represents an aryl group having no substituent on the aromatic ring carbon atom adjacent to the carbon atom bonded to oxygen atom or an aryl group having a substituent having from 1 to 2 carbon atoms on the aromatic ring carbon atom.

4. The bisphosphite compound according to claim 3, wherein each of $R^1$, $R^{11}$, $R^3$ and $R^{13}$ independently represents a tertiary alkyl group having from 4 to 7 carbon atoms and each of $R^4$ and $R^{14}$ independently represents an alkyl group having from 1 to 3 carbon atoms.

5. The bisphosphite compound according to claim 4, wherein each of $Z^1$ to $Z^4$ independently represents a 1-naphthyl group or a 2-naphthyl group.

6. The bisphosphite compound according to claim 5, wherein $R^1$, $R^{11}$, $R^3$ and $R^{13}$ represent a tert-butyl group and $R^4$ and $R^{14}$ represent a methyl group.

7. A catalyst comprising a complex of the bisphosphite compound according to claim 1 and a metal of Groups 8 to 10.

8. The catalyst according to claim 7, wherein a molar ratio of the bisphosphite compound to the metal of Groups 8 to 10 is from 0.00004 to 500.

9. The catalyst according to claim 7, wherein a molar ratio of the bisphosphite compound to the metal of Groups 8 to 10 is from 0.0002 to 100.

10. The catalyst according to claim 7, wherein a molar ratio of the bisphosphite compound to the metal of Groups 8 to 10 is from 0.001 to 50.

11. A method for producing aldehydes, comprising reacting an olefin compound with carbon monoxide and hydrogen in the presence of a compound of a metal of Groups 8 to 10 and the bisphosphite compound according to claim 1.

12. The production method of aldehydes according to claim 11, wherein a concentration of the compound of a metal of Groups 8 to 10 in a reaction solution is from 0.05 to 5,000 mg/L in terms of metal atoms.

13. A method for producing aldehydes, comprising reacting an olefin compound with carbon monoxide and hydrogen in the presence of the catalyst according to claim 7.

14. A method for producing an alcohol, comprising producing aldehydes by the production method of aldehydes according to claim 11, and then reacting the aldehydes with hydrogen.

15. A method for producing an alcohol, comprising producing aldehydes by the production method of aldehydes according to claim 13, and then reacting the aldehydes with hydrogen.

\* \* \* \* \*